US008835621B2

(12) United States Patent
Reed

(10) Patent No.: US 8,835,621 B2
(45) Date of Patent: Sep. 16, 2014

(54) SYNTHETIC 5'UTRS, EXPRESSION VECTORS, AND METHODS FOR INCREASING TRANSGENE EXPRESSION

(75) Inventor: Thomas Reed, Arlington, VA (US)

(73) Assignee: Intrexon Corporation, Blackburg, VA (US)

( * ) Notice: Subject to any disclaimer, the term of this patent is extended or adjusted under 35 U.S.C. 154(b) by 923 days.

(21) Appl. No.: 12/681,609

(22) PCT Filed: Sep. 26, 2008

(86) PCT No.: PCT/US2008/078028

§ 371 (c)(1),
(2), (4) Date: Jul. 29, 2010

(87) PCT Pub. No.: WO2009/042971

PCT Pub. Date: Apr. 2, 2009

(65) Prior Publication Data

US 2010/0293625 A1 Nov. 18, 2010

Related U.S. Application Data

(60) Provisional application No. 60/975,407, filed on Sep. 26, 2007.

(51) Int. Cl.

| | |
|---|---|
| ***C12N 15/63*** | (2006.01) |
| ***C12N 15/10*** | (2006.01) |
| ***C12N 15/64*** | (2006.01) |
| ***C12N 15/85*** | (2006.01) |

(52) U.S. Cl.

USPC ..... 536/24.1; 435/320.1; 435/69.1; 435/91.4; 435/325

(58) Field of Classification Search

CPC ........... C12N 2830/42; C12N 2840/44; C12N 15/8216; C12N 2800/107; C12N 15/63; C12N 15/85; C12N 15/64; C12N 2830/34; C12N 2800/00; C07K 14/4732; C07K 2319/61

See application file for complete search history.

(56) References Cited

U.S. PATENT DOCUMENTS

| | | | | |
|---|---|---|---|---|
| 5,741,957 | A | 4/1998 | Deboer et al. | |
| 6,812,339 | B1 | 11/2004 | Venter et al. | |
| 7,183,395 | B2 | 2/2007 | Mauro et al. | |
| 2003/0181405 | A1 | 9/2003 | Nordstrom et al. | |
| 2003/0211080 | A1 | 11/2003 | Dillmann | |
| 2003/0228297 | A1 | 12/2003 | Chang | |
| 2004/0219580 | A1 | 11/2004 | Dunn et al. | |
| 2004/0234979 | A1 | 11/2004 | Sun et al. | |
| 2005/0198698 | A1 * | 9/2005 | DeBoer et al. | 800/15 |
| 2006/0148742 | A1 | 7/2006 | Kaye et al. | |
| 2006/0276625 | A1 | 12/2006 | Kim et al. | |
| 2007/0111240 | A1 | 5/2007 | Cox, III | |
| 2007/0130645 | A1 | 6/2007 | Wu et al. | |
| 2008/0124762 | A1 * | 5/2008 | Handa et al. | 435/69.1 |
| 2009/0098055 | A1 * | 4/2009 | Beech et al. | 424/9.2 |
| 2010/0221349 | A1 * | 9/2010 | Fuller | 424/490 |

FOREIGN PATENT DOCUMENTS

| | | | |
|---|---|---|---|
| WO | WO 93/25567 | A1 | 12/1993 |
| WO | WO 2009/025866 | A1 | 2/2009 |

OTHER PUBLICATIONS

Evans, P.D. et al. Litmus 38i (1995) Biotechniques, 19, 130-135.*

Guo et al, Protein tolerance to random amino acid change, PNAS, 2004, vol. 101 (25), pp. 9205-9210.*

Lesk et al, Prediction of Protein Function from Protein Sequence and Structure, p. 27 and 28, downloaded Sep. 16, 2007.*

Choi, T. et al., "A Generic Intron Increase Gene Expression in Transgenic Mice," *Molecular and Cellular Biology 11*:3070-3074, American Society for Microbiology, Washington, D.C., USA (1991).

Gorodetsky, S.I. et al., "Isolation and Characterization of the *Bos taurus* β-casein gene," *Gene 66*: 87-96, Elsevier, Amsterdam, The Netherlands (1988).

Huang, M. and Gorman, C., "Intervening sequences increase efficiency of RNA 3' processing and accumulation of cytoplasmic RNA," Nucleic Acids Res. 18:937-947, Oxford University Press, United Kingdom (1990).

Simons, G., et al., "Overproduction of bovine beta-casein in *Escherichia coli* and engineering of its main chymosin cleavage site," *Protein Eng. 6*:763-770, Oxford University Press, United Kingdom (1993).

Lindblad-Toc, K. et al., "*Canis lupus* familiaris chromosome 26, CanFam3.1, whole genome shotgun sequence," Accession No. NC_006608, retrieved Jul. 9, 2013 from ncbi.nlm.nih.gov/nuccore/NC_006608 (2005).

The *C. elegans* Sequencing Consortium, "Genome Sequence of the Nematode *C. elegans*: A Platform for Investigating Biology," *Science 282*:2012-2018, American Association for the Advancement of Science, United States (1998).

Lytton, J. and D. H. MacLennan, "Molecular Cloning of cDNAs from Human Kidney Coding for Two Alternatively Spliced Products of the Cardiac $Ca^{2+}$-ATPase Gene," *J. Biol. Chem. 263*: 15024-15031, American Soc. Biochem. Mol. Biol. (1988).

* cited by examiner

*Primary Examiner* — Maria Marvich

(74) *Attorney, Agent, or Firm* — Sterne, Kessler, Goldstein & Fox P.L.L.C.

(57) ABSTRACT

The present invention provides synthetic 5'UTRs comprising a first polynucleotide fragment and a second polynucleotide fragment, wherein the first polynucleotide fragment comprises at least one splice site of a first eukaryotic gene, the second polynucleotide fragment comprises at least a portion of 5' untranslated region of a second eukaryotic gene, and the first polynucleotide fragment is located 5' of the second polynucleotide fragment. In one embodiment, the first polynucleotide fragment comprises the second intron of a sarcoplasmic/endoplasmic reticulum calcium ATPase gene and the second polynucleotide fragment comprises at least a portion of the 5' untranslated region (5'UTR) of a eukaryotic casein gene. The synthetic 5'UTRs are useful for increasing the expression of a transgene when positioned between a promoter and a transgene within an expression vector. The present invention also provides vectors comprising synthetic 5'UTRs and methods for increasing the expression of a transgene using synthetic 5'UTRs.

13 Claims, 15 Drawing Sheets

SEQ ID NO:2 cgaagaaggtgagtaatcttaacatgctcttttttttttttttgctaatccctttgtgtgctgatgttaggatgacatttac
aacaaatgtttgttcctgacaggaaaaaccttgctg

SEQ ID NO:4 cgaagaaggtgagtaatcttaacatgttctttttttttttttttttaatccctttgtgtgctgatgttaggatgacatttaca
acaaatgtttgttcctgacaggaaaaaccttgctg

SEQ ID NO:5 agttaccggctgaagaaggtaatcttaacatgctgtttctgtttttttcctctgttggtgtgctgatggtaagatgacagt
taaaacacatgtgtttgtttcttacaggaaaaaccttgctggaacttgtgattgagcagtttgaagacttgctagttagg
attttattactggcagcatgtatatctttt

SEQ ID NO:6 aattgccggctgaagaaggtaaataatattaacatgttattttggagagatgatgtgtgcaggctgattgatgtggaca
attgaaacaaatggtttgtttttttttttttttttttcctttcctttctaacaggaaaaaccttgctggaacttgtgattgagc
agtttgaagacttactagttagaattttactgctggcagcatgtatatctttc

FIGURE 1C

Figures 2A, 2B:
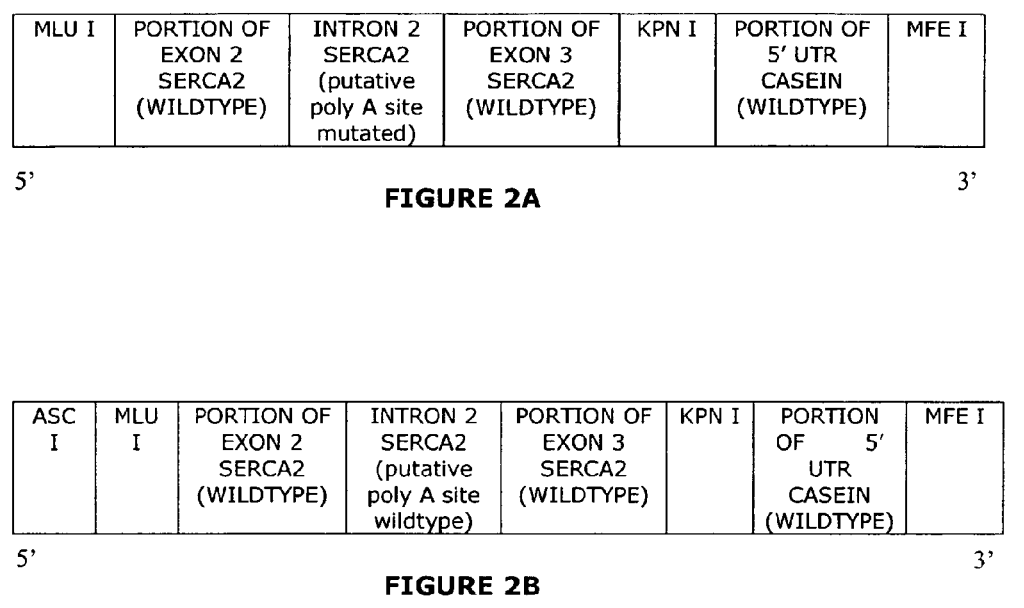

| | | | | | | |
|---|---|---|---|---|---|---|
| MLU I | PORTION OF EXON 2 SERCA2 (WILDTYPE) | INTRON 2 SERCA2 (putative poly A site mutated) | PORTION OF EXON 3 SERCA2 (WILDTYPE) | KPN I | PORTION OF 5′ UTR CASEIN (WILDTYPE) | MFE I |

| | | | | | | | |
|---|---|---|---|---|---|---|---|
| ASC I | MLU I | PORTION OF EXON 2 SERCA2 (WILDTYPE) | INTRON 2 SERCA2 (putative poly A site wildtype) | PORTION OF EXON 3 SERCA2 (WILDTYPE) | KPN I | PORTION OF 5′ UTR CASEIN (WILDTYPE) | MFE I |

Test in HEK293 Cells

| VVN ID# | VEC ID# | Size (bp) | Conc (ug/uL) | Relative Light Units (RLU) | | | | AVG RLU | STDev | Normalized RLU | 5' UTR |
|---|---|---|---|---|---|---|---|---|---|---|---|
| VVN-8276 | VEC-3159 | 8001 bp | 0.5 | 39.24 | 32.802 | 34.227 | 32.15 | 34.6038 | 3.2106 | 21.9042 | INXN-1 |
| VVN-8318 | VEC-3295 | 7844 bp | 0.5 | 4.5651 | 4.9187 | 4.0627 | 4.731 | 4.5695 | 0.3674 | 2.9519 | polyG (12) |
| VVN-8277 | VEC-3164 | 8011 bp | 0.5 | 39.77 | 36.636 | 31.986 | 39.4 | 36.9478 | 3.5912 | 23.3880 | 5U2 (INXN-1-pA-mut 1) |
| VVN-2712 (Pos) | VEC-3386 | 8540 bp | 0.5 | 4.1371 | 4.8691 | 4.8263 | 4.415 | 4.5619 | 0.3494 | | |
| VVN-2713 (Neg) | VEC-3387 | 5069 bp | 0.5 | 0.0102 | 0.0157 | 0.0195 | 0.014 | 0.0149 | 0.0038 | | |

Test in 1080 Cells

| VVN ID# | VEC ID# | Size (bp) | Conc (ug/uL) | Relative Light Units (RLU) | | | | AVG RLU | STDev | Normalized RLU | 5' UTR |
|---|---|---|---|---|---|---|---|---|---|---|---|
| VVN-8276 | VEC-3159 | 8001 bp | 0.5 | 374.29 | 325.22 | 343.81 | 388.3 | 357.9040 | 28.6318 | 226.5532 | INXN-1 |
| VVN-8318 | VEC-3295 | 7844 bp | 0.5 | 140.92 | 148.52 | 142.94 | 149.3 | 145.4223 | 4.1338 | 93.9428 | polyG (12) |
| VVN-8277 | VEC-3164 | 8011 bp | 0.5 | 383.31 | 394.92 | 369.89 | 406.7 | 388.7005 | 15.7617 | 246.0474 | INXN-1 (pA-mut 1)=5U2 |
| VVN-2712 (Pos) | VEC-3386 | 8540 bp | 0.5 | 89.46 | 80.038 | 72.098 | 74.14 | 78.9333 | 7.7837 | | |
| VVN-2713 (Neg) | VEC-3387 | 5069 bp | 0.5 | 0.1789 | 0.2671 | 0.1681 | 0.167 | 0.1952 | 0.0482 | | |

FIGURE 12

```
281  ---------------------------------------------------------------------------------------------------------------------------ag 282
                                                                                                                                ||
1251 gtctaggtgtgtctttcaaagacagcgatgattttaggaattctttttagaaagatagagtgctaacgtgtttttttcccccccctctggacacgttgcctggcgaatttctacatcctgcagag 1375
            1260     .    1280     .    1300     .    1320     .    1340     .    1360     .
              .                                                                                 300    .   320
283  ttaccggctgaaga---------------------------------------------------------------------------------agggaaaaccttgctggaacttgtgattgag 327
     ||||||||||||||                                                                                ||||||||||||||||||||||||||||||
1376 ttaccggctgaagaaggtgagcgatctgaacgtgttcttcccccgctttgtgctgatgttaagatgacgtttacaacagatgtttgtttctaacagggaaaaccttgctggaacttgtgattgag 1500
      1380     . ↑  1400     .    1420     .    1440     .    1460     . ↑  1480     .    1500
        .    340     .    360     .    380
328  cagtttgaagacttactagttagaattttattgctggcagcatgtatatctttt----------------------------------------------------------------------- 381
     ||||||||||||||||||||||||||||||||||||||||||||||||||||||
1501 cagtttgaagacttactagttagaattttattgctggcagcatgtatatcttttgtaagtataaagaaatttattttgtctccaaaaagttgggaccgttccatagatgaaaagcggggaaagta 1625
             .    1520     .    1540     .    1560     .    1580     .    1600     .    1620
```

(SEQ ID NO: 15)
(SEQ ID NO: 16)

FIGURE 13

SYNTHETIC 5'UTRS, EXPRESSION VECTORS, AND METHODS FOR INCREASING TRANSGENE EXPRESSION

REFERENCE TO SEQUENCE LISTING SUBMITTED ELECTRONICALLY VIA EFS-WEB

This application includes a "Sequence_Listing.txt," 35,708 bytes, created on Apr. 25, 2013, and submitted electronically via EFS-Web, which is hereby incorporated by reference in its entirety.

BACKGROUND OF THE INVENTION

1. Field of the Invention

This invention is in the field of biotechnology. In particular, it relates to improvements in the post-transcriptional control of gene expression in eukaryotic cells.

2. Background of the Invention

Eukaryotic gene expression undergoes several points of control after transcription of primary mRNA from DNA. The primary mRNA transcript is comprised of coding portions (exons) and non-coding portions (introns). During mRNA splicing, introns are cut and removed from the transcript and exons are joined together to generate mature messenger RNA (mRNA). Splicing serves as a point of control for generating multiple protein isoforms from a single gene through the addition and removal of exons in various combinations. This process, termed alternative splicing, occurs within tightly regulated, multi-component structures called spliceosomes, which are under the control of intra- and extra-cellular signaling pathways.

Alternative splicing within the coding region of a protein can result in generation of multiple isoforms with diverse functions. Additionally, splicing has been shown to dramatically increase protein synthesis in mammalian cells (Huang and Gorman, 1990 Nucleic Acids Research 18(4):937-947). The mechanism for this is unknown. Alternative splicing can also occur in the untranslated regions of the transcript, which may contribute enhancer or stabilization domains to the final transcript, resulting in increased translation of protein.

Addition of splicing elements in the 5' regulatory region in a synthetic gene construct has been shown to increase gene expression, theoretically as a result of improved mRNA transport from the nucleus to the cytoplasm (Huang and Gorman, supra; Choi et al., 1991 Molecular and Cellular Biology 11(6):3070-3074). As a result of this work, introns are often included between the promoter and multiple cloning site of commercially available mammalian expression vectors. However, combinations of introns with other regulatory regions have not been evaluated for increasing gene expression.

SUMMARY OF THE INVENTION

The present invention provides synthetic 5'UTR polynucleotide sequences that are designed to increase the expression of a transgene component of a synthetic gene construct in a host cell. Not being bound by theory, the synthetic 5'UTRs are designed so that expression of a transgene may be increased through increased RNA transport and stability.

The synthetic 5'UTR sequences comprise a polynucleotide fragment comprising a splice site from a first eukaryotic gene fused to a polynucleotide fragment encoding a 5'UTR sequence of a second eukaryotic gene that is stable at the RNA and protein levels. In one embodiment, the synthetic 5'UTR sequence is a chimeric sequence comprising a polynucleotide fragment comprising a splice site of a sarcoplasmic/endoplasmic reticulum calcium ATPase gene and a polynucleotide fragment comprising at least a portion of a 5'UTR of a casein gene.

The synthetic 5'UTR polynucleotide sequences of the invention have utility for increasing the expression of a sequence of interest or coding region of interest within a synthetic gene construct. The synthetic 5'UTR sequence may be inserted into viral or non-viral vectors between a promoter and a nucleotide sequence of interest using recombinant DNA techniques. The synthetic 5'UTR sequences are optionally flanked by nucleotide sequences comprising restriction endonuclease sites and other nucleotides needed for restriction endonuclease activity. The flanking sequences optionally provide cloning sites within a vector.

The present invention also provides vectors comprising synthetic 5'UTRs. In one embodiment of the invention, the vector is a eukaryotic expression vector.

The present invention also provides methods for increasing the expression of a transgene in a eukaryotic cell. The methods comprise the steps of creating a synthetic 5'UTR sequence by fusing a polynucleotide fragment of a first eukaryotic gene comprising a splice site and a polynucleotide fragment of a second eukaryotic gene comprising at least a portion of a 5'UTR to create a chimeric polynucleotide sequence, and inserting the chimeric polynucleotide sequence within an expression vector between a promoter and a sequence of interest.

Applicant has made the surprising discovery that a synthetic 5'UTR sequence created by fusing a polynucleotide fragment comprising an intron of a sarcoplasmic/endoplasmic reticulum calcium ATPase gene with a polynucleotide fragment comprising at least a portion of a casein gene results in increased gene expression. As described in detail herein, two different embodiments of a synthetic 5'UTR increased the expression of a reporter gene, compared to control, in two different cell types transfected with an expression vector comprising the synthetic 5'UTR.

Thus, it is one object of the invention to provide a synthetic 5'UTR sequence comprising a polynucleotide fragment comprising a splice site fused to a polynucleotide fragment comprising at least a portion of a heterologous 5' untranslated region for increasing the expression of a transgene in a eukaryotic cell.

It is another object of the invention to provide a synthetic 5'UTR sequence comprising a polynucleotide fragment comprising an intron fused to a polynucleotide fragment comprising at least a portion of a heterologous 5' untranslated region for increasing the expression of a transgene in a eukaryotic cell.

It is another object of the invention to provide a synthetic 5'UTR sequence comprising a polynucleotide fragment comprising an intron that includes flanking 5' and 3' portions of neighboring exons fused to a polynucleotide fragment comprising at least a portion of a heterologous 5' untranslated region for increasing the expression of a transgene in a eukaryotic cell.

It is another object of the invention to provide a synthetic 5'UTR sequence that is compatible for insertion into a vector.

It is another object of the invention to provide vectors comprising synthetic 5'UTRs.

It is another object of the invention to provide host cells comprising synthetic 5'UTRs.

DESCRIPTION OF THE SEQUENCES

SEQ ID NO:1 represents an embodiment of a synthetic 5'UTR sequence comprising: MluI restriction site, SEQ ID NO:2, KpnI restriction site, SEQ ID NO:3, MfeI restriction site. SEQ ID NO:1 is also known herein as 5U2.

SEQ ID NO:2 represents an embodiment of a canine SERCA2 intron 2 sequence with a mutated putative consensus poly-A site, with a portion of exon 2 flanking on the 5' end and a portion of exon 3 flanking on the 3' end. SEQ ID NO:2 is a mutated partial sequence of *Canis familiaris* chromosome 26, whole genome shotgun sequence (public accession number NC_006608.2).

SEQ ID NO:3 represents an embodiment of a bovine casein 5'UTR sequence. SEQ ID NO:3 is a partial sequence of the full length *Bos taurus* casein beta mRNA (public accession number NM_181008).

SEQ ID NO:4 represents an embodiment of a canine wild-type SERCA2 intron 2 sequence, with a portion of exon 2 flanking on the 5' end and a portion of exon 3 flanking on the 3' end. SEQ ID NO:4 is a partial sequence of *Canis familiaris* chromosome 26, whole genome shotgun sequence (public accession number NC_006608.2).

SEQ ID NO:5 represents an embodiment of a human wild-type SERCA2 intron 2 sequence, with exon 2 flanking on the 5' end and exon 3 flanking on the 3' end. SEQ ID NO:5 is a partial sequence of *Homo sapiens* chromosome 12, reference assembly, complete sequence (public accession number NC_000012).

SEQ ID NO:6 represents an embodiment of a mouse wild-type SERCA2 intron 2 sequence, with exon 2 flanking on the 5' end and exon 3 flanking on the 3' end. SEQ ID NO:6 is a partial sequence of *Mus musculus* chromosome 5, reference assembly (public accession number NC_000071).

SEQ ID NO:7 represents an embodiment of a synthetic 5'UTR sequence comprising AscI restriction site, MluI restriction site, SEQ ID NO:4, KpnI restriction site, SEQ ID NO:3, MfeI restriction site. SEQ ID NO:7 is also known herein as INXN-1.

SEQ ID NO:8 represents an embodiment of a mouse casein 5'UTR sequence. SEQ ID NO:8 is a partial sequence of *Mus musculus* casein beta, mRNA (cDNA clone MGC:91065) (public accession number BC080709).

SEQ ID NO:9 represents an embodiment of a rat casein 5'UTR sequence. SEQ ID NO:9 is a partial sequence of *Rattus norvegicus* casein beta (Csn2), mRNA (public accession number NM_017120).

SEQ ID NO:10 represents an embodiment of a sheep casein 5'UTR sequence. SEQ ID NO:10 is a partial sequence of *Ovis aries* casein beta (CSN2), mRNA, (public accession number NM_001009373).

SEQ ID NO:11 represents exon 3 of canine SERCA2. SEQ ID NO:11 is a partial sequence of *Canis familiaris* chromosome 26, whole genome shotgun sequence (public accession number NC_006608.2).

SEQ ID NO:12 represents an embodiment of a vector sequence comprising a synthetic 5'UTR. The vector represented by SEQ ID NO:12 comprises SEQ ID NO:1 and is depicted schematically in FIG. 10.

SEQ ID NO:13 represent another embodiment of a vector sequence comprising a synthetic 5'UTR. The vector represented by SEQ ID NO:13 comprises SEQ ID NO:7 and is depicted schematically in FIG. 11.

SEQ ID NO:14 represents a vector comprising a control (polyG) synthetic 5'UTR and is depicted schematically in FIG. 9.

In any of these sequences, T (thymidine) can be replace with U (Uracil).

DESCRIPTION OF THE DRAWINGS

FIG. 1C depicts the polynucleotides of SEQ ID NO:2 and SEQ ID NOS:4-6. The second intron of SERCA2 is highlighted in black. Neighboring exons or their portions are unhighlighted.

FIG. 2A depicts a schematic representation of the polynucleotide of SEQ ID NO:1.

FIG. 2B depicts a schematic representation of the polynucleotide of SEQ ID NO:7.

FIG. 12 is a table containing the data of Example 1 depicted in FIGS. 4-6.

FIG. 13 depicts a portion of an alignment of the *Equus caballus* SERCA2 genomic and mRNA sequences that includes the second intron and exon 2 and exon 3. The 5' and 3' ends of the second intron are indicated by arrows.

FIGS. 7-11 use the following abbreviations: CMV pro=Cytomegalovirus promoter, LacZ=LacZ coding sequence, SV40pA=SV40 polyA, Amp=Ampicillin resistance gene, Neo=Neomycin resistance gene, MCS=Multiple Cloning Site, SPL-1=portion of exon 2 SERCA2+ intron 2 SERCA2+ portion of exon 3 SERCA2, UTR-1=portion of 5'UTR casein.

DETAILED DESCRIPTION OF THE INVENTION

Figure 1A:
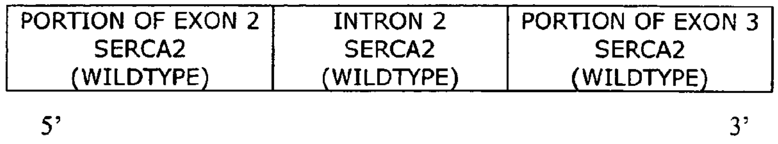
FIG. 1A depicts a schematic representation of the polynucleotide of SEQ ID NO:4.

The following definitions shall apply throughout this description, the drawings, and the claims that follow. However, terms used in the specification and claims not defined herein have ordinary meanings understood in the art.

When the terms "one," "a," or "an" are used in this disclosure, they mean "at least one" or "one or more," unless otherwise indicated.

"Nucleic acid," "nucleic acid molecule," "nucleic acid sequence," "oligonucleotide," "oligonucleotide sequence," "nucleotide sequence," "polynucleotide," and "polynucleotide sequence" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes but is not limited to cDNA, genomic DNA, plasmid DNA, synthetic DNA, and semi-synthetic DNA.

The terms "fragment" used in connection with a polynucleotide sequence (e.g. "polynucleotide fragment") refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, polynucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

The term "chimeric" means comprised of fragments that are not contiguous in their natural state. For example, a chimeric polynucleotide means a polynucleotide comprising fragments that are not contiguous in their natural state.

The term "synthetic" used in connection with a polynucleotide sequenceis a non-natural polynucleotide (or portion of a polynucleotide) that differs from a wildtype polynucleotide sequence. For example, a synthetic gene (or portion of a gene) may contain one or more nucleic acid sequences not contiguous in nature (chimeric sequences), and/or may encompass substitutions, insertions, and deletions and combinations thereof.

A "gene" refers to a polynucleotide comprising nucleotides that encode a functional molecule (e.g., a polypeptide or RNA), and includes cDNA or genomic DNA nucleic acids. It is generally understood that genomic DNA encoding for a polypeptide or RNA includes non-coding regions (i.e. introns) that are spliced from mature mRNA, and are therefore not present in cDNA encoding for the same polypeptide or RNA. "Gene" may comprise a nucleic acid fragment that expresses a specific RNA, protein or polypeptide. The "gene" may further comprise regulatory sequences preceding (5' non-coding sequences) and following (3' non-coding sequences) the coding sequence. The "gene" may also comprise triplex-forming oligonucleotides (TFOs). "Native gene" refers to a gene as found in nature with its own regulatory sequences. "Chimeric gene" or "recombinant gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism.

A "foreign" gene or "exogenous" gene or "heterologous" gene or "transgene" refers to a gene not normally found in the host cell or organism, but that is introduced into the host cell or organism by gene transfer. Transgenes can comprise native genes inserted into a non-native organism, or chimeric or synthetic genes. A transgene may also be a cDNA version of an endogenous gene. A transgene gene may also be an unmutated version of an endogenous mutated gene or a mutated version of an endogenous unmutated gene. A transgene gene may also be a therapeutic gene or an experimental gene such as a reporter. A transgene can be directly introduced into the target cells of a host organism, or indirectly introduced by the transfer of transformed cells, e.g. autologous cells, into the host organism.

The "5 prime untranslated region" or "5'UTR" of a gene is to be understood as that part of a gene which is transcribed into a primary RNA transcript (pre-mRNA) and which part is located upstream of the coding sequence. The primary transcript is the initial RNA product, containing introns and exons, produced by transcription of DNA. Many primary transcripts must undergo RNA processing to form the physiologically active RNA species. The processing into a mature mRNA may comprise trimming of the ends, removal of introns, capping and/or cutting out of individual rRNA molecules from their precursor RNAs. The 5'UTR of an mRNA is thus that part of the mRNA which is not translated into protein and which is located upstream of the coding sequence. In a genomic sequence, the 5'UTR is typically defined as the region between the transcription initiation site and the start codon. The 5' untranslated regions (5'UTRs) of vertebrate mRNAs may be a few tens of bases to several hundred bases in length (Crowe et al., 2006 BMC Genomics 7:16).

A "synthetic 5'UTR" is a non-natural 5'UTR that differs from a wildtype 5'UTR polynucleotide sequence. A synthetic 5'UTR may contain one or more nucleic acid sequences not contiguous in nature (chimeric sequences), and/or may encompass substitutions, insertions, and deletions and combinations thereof.

A "splice junction", "intron-exon splice junction", or "splice site" are regions at the boundaries of an intron in eukaryotic pre-mRNAs recognized by the cell's splicing apparatus where two neighboring exons are joined and the intron is deleted. Splice sites are represented by conserved sequences at the 5' and 3' intron/exon boundaries. For the vast majority of introns, the most conserved sequences are GU flanking the 5' end of the intron and AG flanking at the 3' end. However, exceptions to these consensus sequences are also known such as introns with AU-AC splice sites. The 5' splice site at an intron-exon boundary is known as a "splice donor" site. The 3' splice site at an intron-exon boundary is known as a "splice acceptor" site.

A "spliceosome" is a large ribonucleoprotein complex that serves as the cell's splicing apparatus. The spliceosome is comprised of small nuclear ribonucleoproteins (snRNP) subunits that assemble on a pre-mRNA substrate. The snRNPs are themselves comprised of small nuclear RNAs (snRNAs) and several protein subunits. During the splicing reaction, recognition of splice sites within the pre-mRNA is performed through base-pairing with snRNAs.

"Heterologous" DNA refers to DNA not naturally located in the cell, or in a chromosomal site of the cell. Therefore, the heterologous DNA includes a gene foreign to the cell. "Heterologous" DNA may also include a gene naturally existing in the cell, but located in a non-native location. Furthermore, a "heterologous" DNA molecule may be a DNA molecule containing a non-host DNA segment, operably linked to a host DNA segment, for example, a transcription promoter. Conversely, a heterologous DNA molecule may comprise an endogenous gene operably linked with an exogenous promoter. Further, "heterologous" may refer to a DNA molecule or fragment that is derived from a gene that does not share a common evolutionary origin with a reference DNA molecule or fragment.

The term "genome" includes chromosomal as well as mitochondrial, chloroplast and viral DNA or RNA.

The term "probe" refers to a single-stranded nucleic acid molecule that can base pair with a complementary single stranded target nucleic acid to form a double-stranded molecule.

A DNA "coding sequence" refers to a double-stranded DNA sequence that encodes a polypeptide and can be transcribed and translated into a polypeptide in a cell in vitro or in vivo or outside a cell, e.g., in a tube, when placed under the control of appropriate regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic, eukaryotic, or chimeric sequences, cDNA from mRNA, genomic DNA sequences, and even synthetic DNA sequences.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The terms "restriction endonuclease" and "restriction enzyme" are used interchangeably and refer to an enzyme that binds and cuts within a specific nucleotide sequence within double stranded DNA.

"Polypeptide," "peptide" and "protein" are used interchangeably and refer to a polymeric compound comprised of covalently linked amino acid residues. Amino acids have the following general structure:

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667 (1987)). Such proteins (and their encoding genes) have sequence homology, as reflected by their high degree of sequence similarity. However, in common usage and in the present application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., Cell 50:667 (1987)). In one embodiment, two DNA sequences are "substantially homologous" or "substantially similar" when at least about 21% (preferably at least about 50%, and most preferably at least about 75%, 90%, 95%, 96%, 97%, 98%, or 99%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, infra.).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the present invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. Molecular Cloning. A Laboratory Manual, Second Edition, Cold Spring Harbor Laboratory Press, Cold Spring Harbor (1989), particularly Chapter 11 and Table 11.1 therein. The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a Tm of 55° C., can be used, e.g., S×SSC, 0.1% SDS, 0.25% milk, and no formamide; or 30% formamide, S×SSC, 0.5% SDS. Moderate stringency hybridization conditions correspond to a higher Tm, e.g., 40% formamide, with 5× or 6×SSC. High stringency hybridization conditions correspond to the highest Tm, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In one embodiment, polynucleotides are detected by employing hybridization conditions comprising a hybridization step at Tm of 55° C., and utilizing conditions as set forth above. In another embodiment, the Tm is 60° C.; in certain embodiments, the Tm is 63° C. or 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. Another example of stringent conditions uses higher temperatures in which the washes are identical to those above except for the temperature of the final two 30 min washes in 0.2×SSC, 0.5% SDS was increased to 60° C. Still another example of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment, polynucleotides are detected by employing hybridization conditions comprising a hybridization step in less than 500 mM salt and at least 37° C., and a washing step in 2×SSPE at least 63° C. In another embodiment, the hybridization conditions comprise less than 200 mM salt and at least 37° C. for the hybridization step. In certain embodiments, the hybridization conditions comprise 2×SSPE and 63° C. for both the hybridization and washing steps.

The length for a hybridizable nucleic acid is, for example, at least about 10 nucleotides. A minimum length for a hybridizable nucleic acid may be at least about 15 nucleotides; at least about 20 nucleotides; or at least 30 nucleotides. Furthermore, the skilled artisan will recognize that the temperature and wash solution salt concentration may be adjusted as necessary according to factors such as length of the probe.

Substantially similar nucleic acid fragments of the present invention are those nucleic acid fragments whose DNA sequences are at least 70% identical to the DNA sequence of the nucleic acid fragments reported herein. Nucleic acid fragments of the present invention include those nucleic acid fragments whose DNA sequences are at least 80%, 90%, 95%, 96%, 97%, 98%, and 99% identical to the DNA sequence of the nucleic acid fragments reported herein.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., J. Mol. Biol. 215:403 410 (1993)); BLAST is publicly available on the World Wide Web. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20 to 30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 to 15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent similarity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins et al., CABIOS. 5:151 153 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., J. Mol. Biol. 215:403 410 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

As used herein, the terms "expression" or "gene expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Upregulation" or "activation" refers to regulation that increases the production of gene expression products (i.e., RNA or protein), while "down-regulation" or "repression" refers to regulation that decrease production. Factors (e.g., transcription factors) that are involved in up-regulation or down-regulation are often called "activators" and "repressors," respectively. For the purposes of the invention, a target gene may be down-regulated "post-transcriptionally" (i.e. at the level of the RNA transcript) through specific interaction with a down-regulating RNA molecule.

The term "Transcriptional and translational control sequences" refer to DNA regulatory sequences, such as promoters, enhancers, terminators, and the like, that provide for the expression of a coding sequence in a host cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a host cell in vitro, ex vivo or in vivo. The term "vector" may also include minicircle DNAs. For example, the vector may be a plasmid without bacterial DNA sequences. The removal of bacterial DNA sequences which are rich in CpG regions has been shown to decrease transgene expression silencing and result in more persistent expression from plasmid DNA vectors (see e.g., Ehrhardt, A. et al. (2003) Hum Gene Ther 10: 215-25; Yet, N. S. (2002) Mol Ther 5: 731-38; Chen, Z. Y. et al. (2004) Gene Ther 11: 856-64). The term "vector" may also include transposons such as Sleeping Beauty (Izsvak et al. J. Mol. Biol. 302:93-102 (2000)), or artificial chromosomes.

A large number of vectors known in the art may be used to manipulate nucleic acids, incorporate response elements and promoters into genes, etc. or transfer a nucleic acid into a host cell. Possible vectors include, for example, plasmids or modified viruses including, for example bacteriophages such as lambda derivatives, or plasmids such as pBR322 or pUC plasmid derivatives, or the Bluescript vector. Larger vectors such as artificial chromosomes (bacteria (BAC), yeast (YAC), or human (HAC)) may be used to accommodate larger inserts. For example, the insertion of the DNA fragments corresponding to response elements or promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells transfected or transformed with the vector. A recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify or select a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), fluorescent proteins such as green fluorescent protein (GFP), chloramphenicol acetyltransferase (CAT), beta-galactosidase (LacZ), beta-glucuronidase (Gus), and the like. Selectable marker genes may also be considered reporter genes.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, e.g., DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

The term "expression vector" refers to a vector, plasmid or vehicle designed to enable the expression of an inserted nucleic acid sequence following transformation into a host cell. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the host cell are numerous and familiar to those skilled in the art.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., J. Biol. Chem. 267:963-967 (1992); Wu et al., J. Biol. Chem. 263:14621-14624 (1988); and Hartmut et al., Canadian Patent Application No. 2,012,311, filed Mar. 15, 1990).

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCMVDsRed2-express, pIRES2-DsRed2, pDsRed2-Mito, pCMV-EGFP available from Clontech. Many other vectors are well-known and commercially available.

For example, useful vectors, which comprise molecular insertion pivots for rapid insertion and removal of elements of gene programs, are described in United States Published Patent Application No. 2004/0185556, U.S. patent application Ser. No. 11/233,246 and International Published Application Nos. WO 2005/040336 and WO 2005/116231.

"Promoter" and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions.

Promoters that cause a gene to be expressed in most cell types at most times are commonly referred to as "constitutive promoters." Promoters that cause a gene to be expressed in a specific cell type are commonly referred to as "conditional promoters." Non-limiting examples of conditional promoters are "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." A non-limiting example of the inducible promoter is a TetO inducible promoter. It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

Termination control regions, i.e., terminator or polyadenylation sequences, may also be derived from various genes native to the preferred hosts. Optionally, a termination site may be unnecessary, however, it can be included. In one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The term "transfection" refers to the uptake of exogenous or heterologous RNA or DNA by a cell. A cell has been "transfected" by exogenous or heterologous RNA or DNA when such RNA or DNA has been introduced inside the cell. The transfected RNA or DNA can be integrated (covalently linked) into chromosomal DNA making up the genome of the host cell.

"Transformation" refers to the transfer of a nucleic acid fragment into the genome of a host organism, resulting in genetically stable inheritance.

The terms "modulate" and "modulates" mean to induce, reduce or inhibit nucleic acid or gene expression, resulting in the respective induction, reduction or inhibition of protein or polypeptide production.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell.

One embodiment of the invention is a synthetic 5'UTR polynucleotide comprising a first polynucleotide fragment and a second polynucleotide fragment, wherein:

a. the first polynucleotide fragment comprises at least one splice site of a first eukaryotic gene;
b. the second polynucleotide fragment comprises at least a portion of 5' untranslated region of a second eukaryotic gene; and
c. the first polynucleotide fragment is located 5' of the second polynucleotide fragment.

In another embodiment of the invention, the synthetic 5'UTR is a chimeric polynucleotide comprising a first polynucleotide fragment and a second polynucleotide fragment, wherein:

a. the first polynucleotide fragment comprises the second intron of a sarcoplasmic/endoplasmic reticulum calcium ATPase gene;
b. the second polynucleotide fragment comprises at least a portion of the 5' untranslated region (5'UTR) of a casein gene; and
c. the first polynucleotide fragment is located 5' of the second polynucleotide fragment.

The polynucleotide fragment comprising the second intron of a sarcoplasmic/endoplasmic reticulum calcium ATPase gene may be derived from any eukaryotic sarcoplasmic/endoplasmic reticulum calcium ATPase gene. In one embodiment of the invention, the polynucleotide fragment comprising the second intron of a eukaryotic sarcoplasmic/endoplasmic reticulum calcium ATPase gene is derived from a SERCA2 gene. In other embodiments it is derived from a SERCA1 or SERCA3 gene. The sarcoplasmic/endoplasmic reticulum calcium ATPase gene that is the source of the polynucleotide fragment comprising the second intron may be from any eukaryotic species. In one embodiment, the sarcoplasmic/endoplasmic reticulum calcium ATPase gene is from a mammalian species. In another embodiment, the sarcoplasmic/endoplasmic reticulum calcium ATPase gene is from an avian species. In another embodiment, the sarcoplasmic/endoplasmic reticulum calcium ATPase gene is from a piscine species. In specific embodiments, the polynucleotide fragment comprising the second intron is derived from the sarcoplasmic/endoplasmic reticulum calcium ATPase gene of a human, a dog, or a mouse. In other specific embodiments, the polynucleotide fragment comprising the second intron is derived from the sarcoplasmic/endoplasmic reticulum calcium ATPase gene of a rat, a chimpanzee, a chicken, a horse, a cow, an elk, a pig, a cat, a rhesus macaque, or a zebrafish.

In another embodiment of the invention, the polynucleotide fragment comprising the second intron of a sarcoplasmic/endoplasmic reticulum calcium ATPase gene comprises a portion of exon 2 flanking on the 5' end and a portion of exon 3 flanking on the 3' end. In another embodiment, the polynucleotide fragment comprising the second intron of a sarcoplasmic/endoplasmic reticulum calcium ATPase gene comprises the entirety of exon 2 flanking on the 5' end and the entirety of exon 3 flanking on the 3' end.

The polynucleotide fragment comprising the second intron of a sarcoplasmic/endoplasmic reticulum calcium ATPase gene may be at least about 50 nucleotides in length. In other embodiments, the polynucleotide fragment comprising the second intron of a sarcoplasmic/endoplasmic reticulum calcium ATPase gene may be at least about 60, 70, 80, 90, 100, 110, 120, 130, 140, 150, 160, 170, 180, 190, 200, 210, 220, 230, 240, or 250 nucleotides in length.

In another embodiment of the invention, the polynucleotide fragment comprising the second intron of a sarcoplasmic/endoplasmic reticulum calcium ATPase gene is mutated at a putative consensus poly A site. In another embodiment, the polynucleotide fragment comprising the second intron of a sarcoplasmic/endoplasmic reticulum calcium ATPase gene comprises a 5' flanking portion of exon 2 and a 3' flanking portion of exon 3, is mutated at a putative consensus poly A site, and is derived from a canine SERCA2 gene; in a specific embodiment it is represented by SEQ ID NO:2.

Figure 1B:
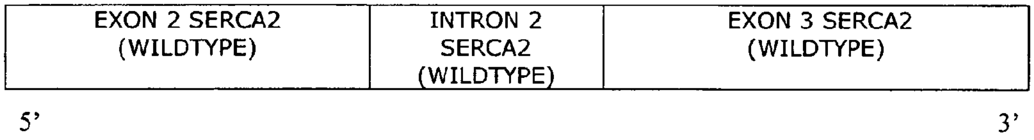
FIG. 1B depicts a schematic representation of the polynucleotide of SEQ ID NO:5 and the polynucleotide of SEQ ID NO:6.

In other embodiments, the polynucleotide fragment comprising the second intron of a sarcoplasmic/endoplasmic reticulum calcium ATPase gene is a wild-type or mutated partial SERCA2 sequence. The polynucleotide fragment may be derived from any full length SERCA2 gene of any species. For example, in one embodiment, the polynucleotide fragment comprising the second intron of a sarcoplasmic/endoplasmic reticulum calcium ATPase gene is a wild-type partial canine SERCA2 genomic sequence that comprises a portion of exon 2 flanking on the 5' end and a portion of exon 3 flanking on the 3' end; in a specific embodiment it is represented by SEQ ID NO:4. SEQ ID NO:4 is depicted schematically in FIG. 1A and FIG. 1C. In another embodiment, the polynucleotide fragment comprising the second intron of a sarcoplasmic/endoplasmic reticulum calcium ATPase gene is a wild-type partial human SERCA2 genomic sequence that comprises exon 2 flanking on the 5' end and exon 3 flanking on the 3' end; in a specific embodiment, it is represented by SEQ ID NO:5. In another embodiment, the polynucleotide fragment comprising the second intron of a sarcoplasmic/endoplasmic reticulum calcium ATPase gene is a wild-type partial murine SERCA2 genomic sequence that comprises exon 2 flanking on the 5' end and exon 3 flanking on the 3' end; in a specific embodiment it is represented by SEQ ID NO:6. SEQ ID NO:5 and SEQ ID NO:6 are represented schematically in FIG. 1B and FIG. 1C. In other embodiments, the polynucleotide fragment comprising the second intron of a sarcoplasmic/endoplasmic reticulum calcium ATPase gene is a mutant or wild-type partial *Rattus norvegicus* SERCA2 sequence, *Equus caballus* SERCA2 sequence, *Bos Taurus* SERCA2 sequence, *Pan troglodytes* SERCA2 sequence, *Felis catus* SERCA2 sequence, *Ortolagus cuniculus* SERCA2 sequence, *Sus scrofa* SERCA2 sequence, *Macaca mulatta* SERCA2 sequence, *Cervus elaphus* SERCA2 sequence, *Gallus gallus* SERCA2 sequence, or *Danio rerio* SERCA2 sequence.

The polynucleotide fragment comprising at least a portion of a casein gene 5' untranslated region may be from any mammalian species. In one embodiment the polynucleotide fragment comprising at least a portion of 5' untranslated region is from a bovine beta-casein gene; in a specific embodiment it is represented by SEQ ID NO:3. In another embodiment the polynucleotide fragment comprising at least a portion of 5' untranslated region is from a mouse beta-casein gene; in a specific embodiment it is represented by SEQ ID NO:8. In another embodiment the polynucleotide fragment comprising at least a portion of 5' untranslated region is from a rat beta-casein gene; in a specific embodiment it is represented by SEQ ID NO:9. In another embodiment the polynucleotide fragment comprising at least a portion of 5' untranslated region is from a sheep beta-casein gene; in a specific embodiment it is represented by SEQ ID NO:10. In other embodiments the polynucleotide fragment comprising at least a portion of 5' untranslated region is from a *Bubalus bubalis* beta-casein gene, a *Capra hircus* beta-casein gene, an *Equus caballus* beta-casein gene, a *Sus scrofa* beta-casein gene, a *Camelus dromedaries*, an *Oryctolagus cuniculus* beta-casein gene, or a *Canis lupus* beta-casein gene.

The polynucleotide fragment comprising at least a portion of a casein gene 5' untranslated region may be at least about 25 nucleotides in length. In other embodiments, the polynucleotide fragment of casein gene comprising at least a portion of the 5'UTR may be at least about 30, 35, 40, 45, 50, 55, 60, 65, 70, 75, 85, 90, 100 or more nucleotides in length. In another embodiment, the polynucleotide fragment comprising at least a portion of a casein gene 5'UTR may represent at least about 50% of the natural 5'UTR sequence. In other embodiments, the polynucleotide fragment comprising at least a portion of a casein gene 5'UTR may represent at least about 55%, 60%, 65%, 70%, 75%, 80%, 85%, 90%, 95% or more of the natural 5'UTR sequence. In another embodiment, the polynucleotide fragment comprising at least a portion of a casein gene 5'UTR may represent the entire natural 5'UTR sequence.

In other embodiments, functional variants of the individual components (the polynucleotide fragment comprising the second intron of a sarcoplasmic/endoplasmic reticulum calcium ATPase gene and the polynucleotide fragment comprising at least a portion of 5'UTR of a casein gene) are used to create a synthetic 5'UTR. Functional variants encompass substitution, insertion and deletion variants and combinations thereof. Substitution variants are those in which at least one base in the nucleotide sequence has been removed and a different base inserted in its place. Insertional variants of a nucleic acid are those in which one or more nucleotides are introduced into a predetermined site in the sequence. Deletion variants of a nucleic acid are characterized by the removal of one or more nucleotides from the nucleic acid. Any combination of substitution(s), deletion(s) or insertion(s) may occur provided that the functionality of the component remains essentially the same, that is, that the functional variant, when used in a synthetic 5'UTR of the present invention, causes increased expression of a sequence of interest, synthetic gene, or transgene.

Further, sequences homologous to the specific embodiments of the polynucleotide fragment comprising the second intron of a sarcoplasmic/endoplasmic reticulum calcium ATPase gene disclosed herein (SEQ ID NO:2, SEQ ID NO:4, SEQ ID NO:5, and SEQ ID NO:6) and sequences homologous to the specific embodiments of the polynucleotide fragment comprising at least a portion of 5'UTR of casein (SEQ ID NO:3, SEQ ID NO:8, SEQ ID NO:9, and SEQ ID NO:10) may be used to build a synthetic 5'UTR. As mentioned previously, suitable sources of a fragment for creating a synthetic 5'UTR include a sarcoplasmic/endoplasmic reticulum calcium ATPase gene of any eukaryotic species and a casein gene of any mammalian species. In one embodiment, the polynucleotide fragment comprising the second intron of a sarcoplasmic/endoplasmic reticulum calcium ATPase gene is derived from an orthologue of canine SERCA2, mouse SERCA2, or human SERCA2. In another embodiment, the polynucleotide fragment comprising at least a portion of the 5'UTR of casein is derived from an orthologue of bovine casein-beta, mouse casein-beta, rat casein-beta, or sheep casein beta.

Methods for the search and identification of sarcoplasmic/endoplasmic reticulum calcium ATPase homologues or casein 5'UTR homologues would be known to persons skilled in the art. Such methods comprise comparison of the sequences represented by SEQ ID NOS:2-6 and 8-10, in a computer readable format, with sequences that are available in public databases available on the World Wide Web such as MIPS, GenBank, or EMBL Nucleotide Sequence Database, using algorithms well known in the art for the alignment or comparison of sequences, such as GAP (Needleman and Wunsch, J. Mol. Biol. 48; 443-453 (1970)), BESTFIT (Miller, W., Myers, E. W. & Lipman, D. J., J. Mol. Biol. 215:403-410 (1990)), FASTA and TFASTA (W. R. Pearson and D. J. Lipman Proc. Natl. Acad. Sci. USA 85:2444-2448 (1988)). The software for performing BLAST analysis is publicly available through the National Centre for Biotechnology Information. Suitable homologues may be identified using BLAST default parameters (BLOSUM62 matrix, gap opening penalty 11 and gap extension penalty 1).

Further, homologues to canine, human, or mouse SERCA2 may also be identified by searching on conserved sequences within the SERCA2 gene. For example, the full sequence of canine exon 3 of SERCA2 such as SEQ ID NO:11 may be used as a query sequence in a BLAST search. It is anticipated that using the exon sequence as the query sequence within the BLAST search will retrieve a higher number of SERCA2 homologues than using a sequence comprising the intron sequence. Similarly, homologues to bovine, mouse, rat, or sheep casein-beta may be identified by using a coding portion as the query sequence.

Analysis of genomic sequences for the identification of sarcoplasmic/endoplasmic reticulum calcium ATPase homologues or casein 5'UTR homologues is also possible. Several algorithms and software tools for the identification of genes in raw DNA sequence are available. Usually these tools combine analysis of statistical parameters in the DNA sequence with homology-based methods for identifying homologous sequences in databases. Although none of these methods alone is reliable enough for a good prediction, the combination of various programs usually gives good results. Well known examples of such tools that are publically available on the World Wide Web include GeneMark (Borodovsky, M. and McIninch J. GeneMark: Parallel Gene Recognition for both DNA Strands. Computers & Chemistry, 17, 123-133 (1993)), Gene Locator and Interpolated Markov Modeler (GLIMMER) (A. L. Delcher et al. Improved microbial gene identification with GLIMMER. Nucleic Acids Research, 27, 4636-4641. (1999)), Gene Recognition and Assembly Internet Link (GRAIL), GenScan (Burge, C. and Karlin, S. Prediction of complete gene structures in human genomic DNA. J. Mol. Biol. 268, 78-94 (1997)), and GeneBuilder (Milanesi L. et al. GeneBuilder: interactive in silico prediction of genes structure. Bioinformatics, 15 (7):612-621 (1999)). A combined analysis may be performed with the TIGR Combiner program (J. E. Allen et al. Computational gene prediction using multiple sources of evidence. Genome Research, 14(1), 142-148 (2004)) that predicts gene models using the output from other annotation software such as GeneMark, GlimmerM, GRAIL, GenScan, and Fgenes. It uses a statistical algorithm to identify patterns of evidence corresponding to gene models.

The second intron of a sarcoplasmic/endoplasmic reticulum calcium ATPase gene can be identified through routine methods such as comparing the gene's genomic DNA sequence with that of its mRNA or cDNA sequence in a pairwise alignment program. Regions of homology represent exons, while intervening sequences that are absent in the cDNA sequence but present in the genomic DNA represent introns. The beginning and end of the intron sequence may be identified through its flanking 5' GT and flanking 3' AG. Using this approach, the canine SERCA2 mRNA sequence represented by public accession number NM_001003214 is useful for identifying introns in a canine SERCA2 genomic sequence, while the human and mouse SERCA2 mRNA sequences (NM_170665 and NM_009722, respectively) may be used to identify introns in their respective genomic sequences.

Sarcoplasmic/endoplasmic reticulum calcium ATPase homologues or casein 5'UTR homologues may also be identified by probing a library of genomic or cDNA fragments of another species. For example, genomic DNA of a species of interest can be fragmented into appropriately-sized fragments for insertion into a chosen vector such as a plasmid or lamda vector. The vector is then digested with an appropriate restriction enzyme and then ligated with the complete mixture of genomic fragments. Bacterial cells are transformed with vector and then plated on agarose plates. Colony or phage plaque DNA is then attached to a membrane. In one embodiment, the fragments represented by SEQ ID NOS:2-6 and 8-10 or portions thereof are used as labeled probes for hybridization to the DNA of a clone of the library that contains a homologous sequence. Similar procedures may be used to screen a cDNA library. Further, homologues may be identified by using the fragments represented by SEQ ID NOS:2-6 and 8-10 or portions thereof as labeled probes for a genomic or cDNA Southern hybridization experiment. In other embodiments, more conserved sequences such as those comprising a coding region of a sarcoplasmic/endoplasmic reticulum calcium ATPase gene (such as SEQ ID NO:11) or a casein gene or a portion thereof are used as probes in a Southern hybridization experiment or for screening a library.

Appropriate hybridization conditions may be chosen to permit hybridization of a fragment with a probe from another species (partially mismatched probe-target hybrids) by reducing the stringency of the hybridization experiment through an appropriate combination of temperature, salt concentration, or % formamide. For example, stringency of the hybridization experiment can be lowered by reducing the temperature of increasing the salt concentration. Procedures for identifying appropriate hybridization conditions are well known in the art and are described in Sambrook (2001) Molecular Cloning: a laboratory manual, 3rd Edition Cold Spring Harbor Laboratory Press, CSH, New York.

Another embodiment of the invention is a polynucleotide at least 80%, 85%, 90%, 95%, 96%, 97%, 98% or 99% identical to a polynucleotide represented by one of SEQ ID NOS:1-10.

Another embodiment of the invention is a synthetic 5'UTR comprising a polynucleotide represented by one of SEQ ID NOS:2 and 4-6 and a polynucleotide represented by one of SEQ ID NOS:3 and 8-10.

Another embodiment of the invention is a synthetic 5'UTR comprising a polynucleotide that is at least 80%, 85%, 90%, 95%, 96%, 97%, 98% or 99% identical to a polynucleotide represented by one of SEQ ID NOS:2 and 4-6 and a polynucleotide that is at least 80%, 85%, 90%, 95%, 96%, 97%, 98% or 99% identical to a polynucleotide represented by one of SEQ ID NOS:3, and 8-10.

Another embodiment of the invention is a synthetic gene construct comprising a polynucleotide that is at least 80%, 85%, 90%, 95%, 96%, 97%, 98% or 99% identical to a polynucleotide represented by SEQ ID NO:1.

Another embodiment of the invention is a synthetic gene construct comprising a polynucleotide that is at least 80%, 85%, 90%, 95%, 96%, 97%, 98% or 99% identical to a polynucleotide represented by SEQ ID NO:7.

In another embodiment, the synthetic 5'UTR sequence lacks restriction sites that would interfere with insertion into the UltraVector Production System (Intrexon Corp., Blacksburg, Va.) as described in WO 2007/038276, incorporated herein by reference. In a specific embodiment, the synthetic 5'UTR sequence lacks internal recognition sequences for the following restriction endonucleases: AsiS I, Pac I, Sbf I, Fse I, Asc I, Mlu I, SnaB I, Not I, Sal I, Swa I, Rsr II, BsiW I, Mfe I, Nhe I, Nsi I, Cla I, Nde I, Nsi I, Kpn I, Nco I and Pst I.

The synthetic 5'UTR sequence optionally includes restriction sites at the 5' and 3' end to facilitate cloning into a vector. In a specific embodiment, the synthetic 5'UTR sequence includes recognition sequences for Mlu I at the 5' end and recognition sequences for Mfe I at the 3' end.

In a specific embodiment, the synthetic 5'UTR is represented by SEQ ID NO: 1. SEQ ID NO:1 comprises the following features: MluI restriction site, SEQ ID NO:2, KpnI restriction site, SEQ ID NO:3, MfeI restriction site. SEQ ID NO:1 is represented schematically by FIG. 2A.

In another specific embodiment, the synthetic 5'UTR is represented by SEQ ID NO:7. SEQ ID NO:7 comprises the following features: AscI restriction site, MluI restriction site, SEQ ID NO:4, KpnI restriction site, SEQ ID NO:3, MfeI restriction site. SEQ ID NO:7 is represented schematically by FIG. 2B.

In one embodiment, the synthetic 5'UTR sequence is less than about 500 nucleotides in length. In another embodiment, the synthetic 5'UTR sequence is less than about 400 nucleotides in length. In another embodiment, the synthetic 5'UTR sequence is less than about 350 nucleotides in length. In another embodiment, the synthetic 5'UTR sequence is less than about 300 nucleotides in length. In another embodiment, the synthetic 5'UTR sequence is less than about 240 nucleotides in length. In another embodiment, the synthetic 5'UTR sequence is less than about 200 nucleotides in length.

In another embodiment of the invention, the synthetic 5'UTR polynucleotide is a component of a eukaryotic expression vector, comprising a first polynucleotide fragment and a second polynucleotide fragment, wherein:

a. the first polynucleotide fragment comprises at least one splice site of a first eukaryotic gene;
b. the second polynucleotide fragment comprises at least a portion of 5' untranslated region (5'UTR) of a second eukaryotic gene; and
c. the first polynucleotide fragment is located 5' of the second polynucleotide fragment.

In one embodiment, the polynucleotide fragment comprising at least one splice site is a fragment of a eukaryotic sarcoplasmic/endoplasmic reticulum calcium ATPase gene described herein. In another embodiment, the polynucleotide fragment comprising at least a portion of 5' untranslated region is a fragment of a casein gene described herein.

The present invention also provides vectors comprising a synthetic 5'UTR described herein. The vectors are contemplated to include any of the embodiments of the synthetic 5'UTR polynucleotide sequences described herein. For example, an embodiment of the invention is a vector comprising a synthetic 5'UTR polynucleotide sequence comprising a polynucleotide fragment comprising the second intron of a eukaryotic sarcoplasmic/endoplasmic reticulum calcium ATPase gene and a polynucleotide fragment comprising at least a portion of a 5'UTR of a casein gene.

Another embodiment of the invention is a vector comprising a polynucleotide that is at least 80%, 85%, 90%, 95%, 96%, 97%, 98% or 99% identical to a polynucleotide represented by one of SEQ ID NOS:1-10.

In another embodiment, the vector is an expression vector comprising a synthetic gene construct comprising a synthetic 5'UTR. The synthetic gene construct may comprise a promoter flanking on one end of the synthetic 5'UTR and a sequence of interest to be expressed flanking on the other end of the synthetic 5'UTR. The synthetic gene construct may further comprise a polyadenylation site.

For example, another embodiment of the invention is an expression vector comprising a synthetic gene construct comprising, as arranged from 5' to 3', a promoter, a chimeric polynucleotide, and a sequence of interest to be expressed, wherein:

a. the chimeric polynucleotide comprises a polynucleotide fragment of a first eukaryotic gene comprising at least one splice site and a polynucleotide fragment of a second eukaryotic gene comprising at least a portion of 5' untranslated region; and
b. the chimeric polynucleotide is positioned between the promoter and the sequence of interest to be expressed, wherein the polynucleotide fragment of the first eukaryotic gene is positioned toward the promoter and polynucleotide fragment of the second eukaryotic gene is positioned toward the sequence of interest to be expressed.

Figure 3A:
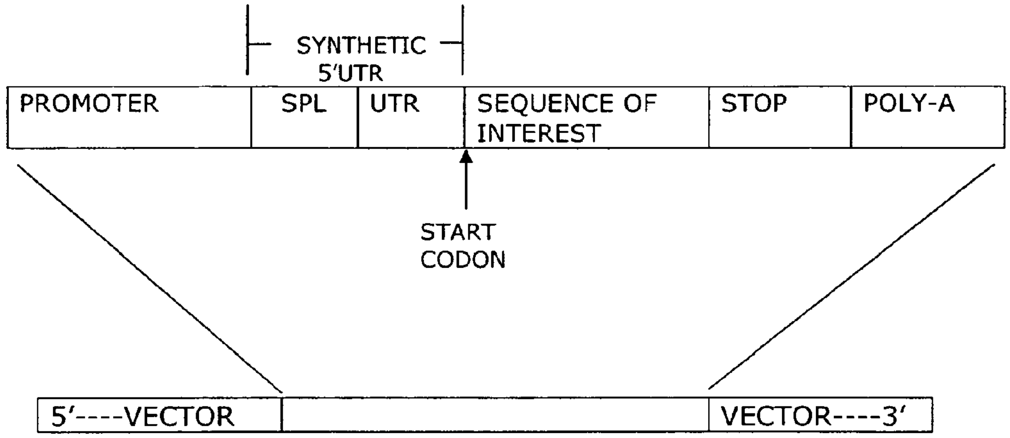
FIG. 3A depicts a schematic representation of a synthetic 5'UTR inserted into an expression vector between a promoter and a sequence of interest.

FIG. 3A schematically represents an embodiment of a synthetic gene construct of the invention inserted into a vector backbone. In this embodiment, SPL in FIG. 3A refers to the polynucleotide fragment comprising at least one splice site and UTR refers to the polynucleotide fragment comprising at least a portion of a 5' untranslated region. SPL and UTR together make up a synthetic 5'UTR. The promoter of the synthetic gene construct is positioned to direct RNA expression of the synthetic 5'UTR and the sequence of interest. Further, the sequence of interest to be expressed comprises a start codon for translation to begin.

Figure 10:
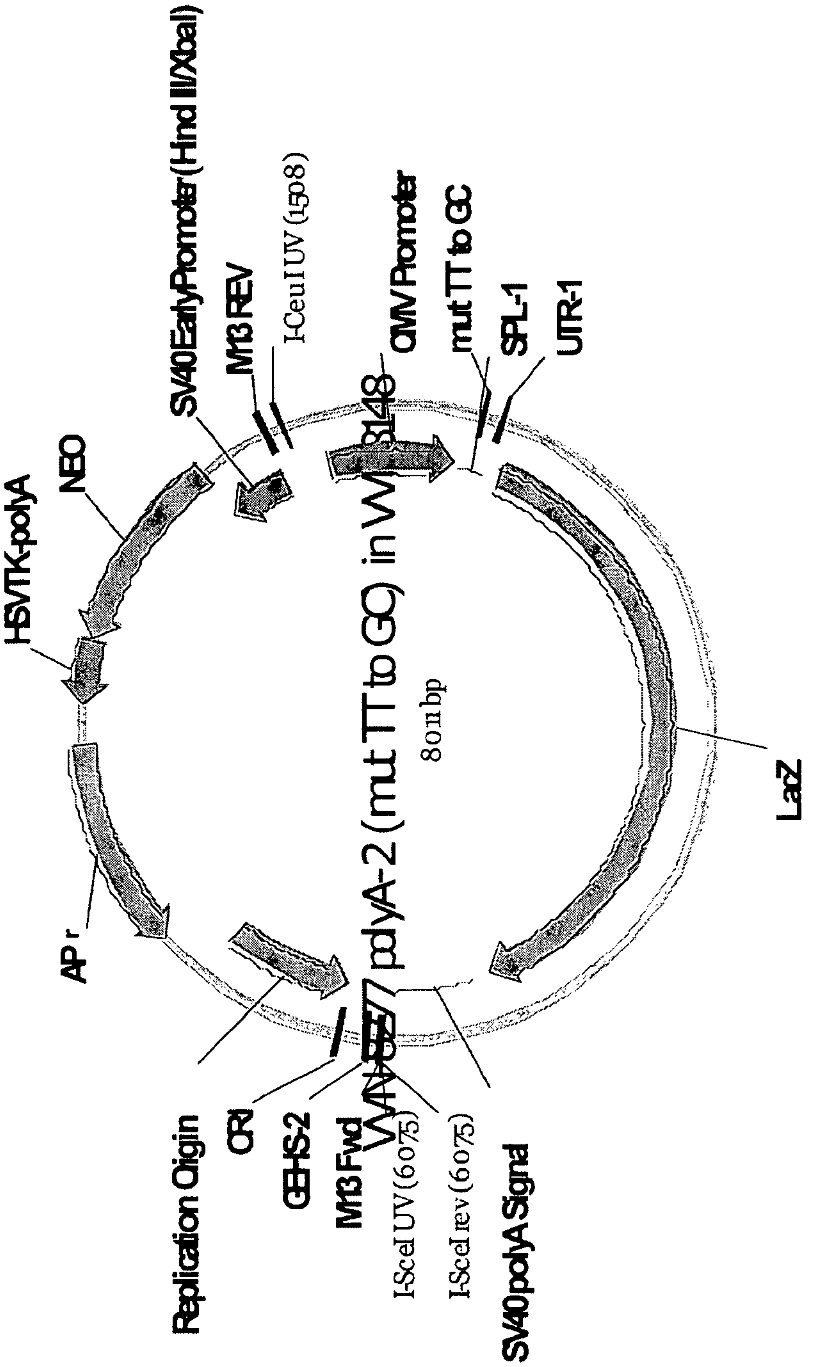
FIG. 10 depicts a vector used in Example 1 (VVN-8277), wherein beta-galactosidase (LacZ) coding sequence is operably linked to a 5'UTR of the invention (5U2) and the CMV promoter.

Exemplary expression vectors comprising this vector architecture are depicted schematically in FIG. 10 and FIG.

Figure 11:
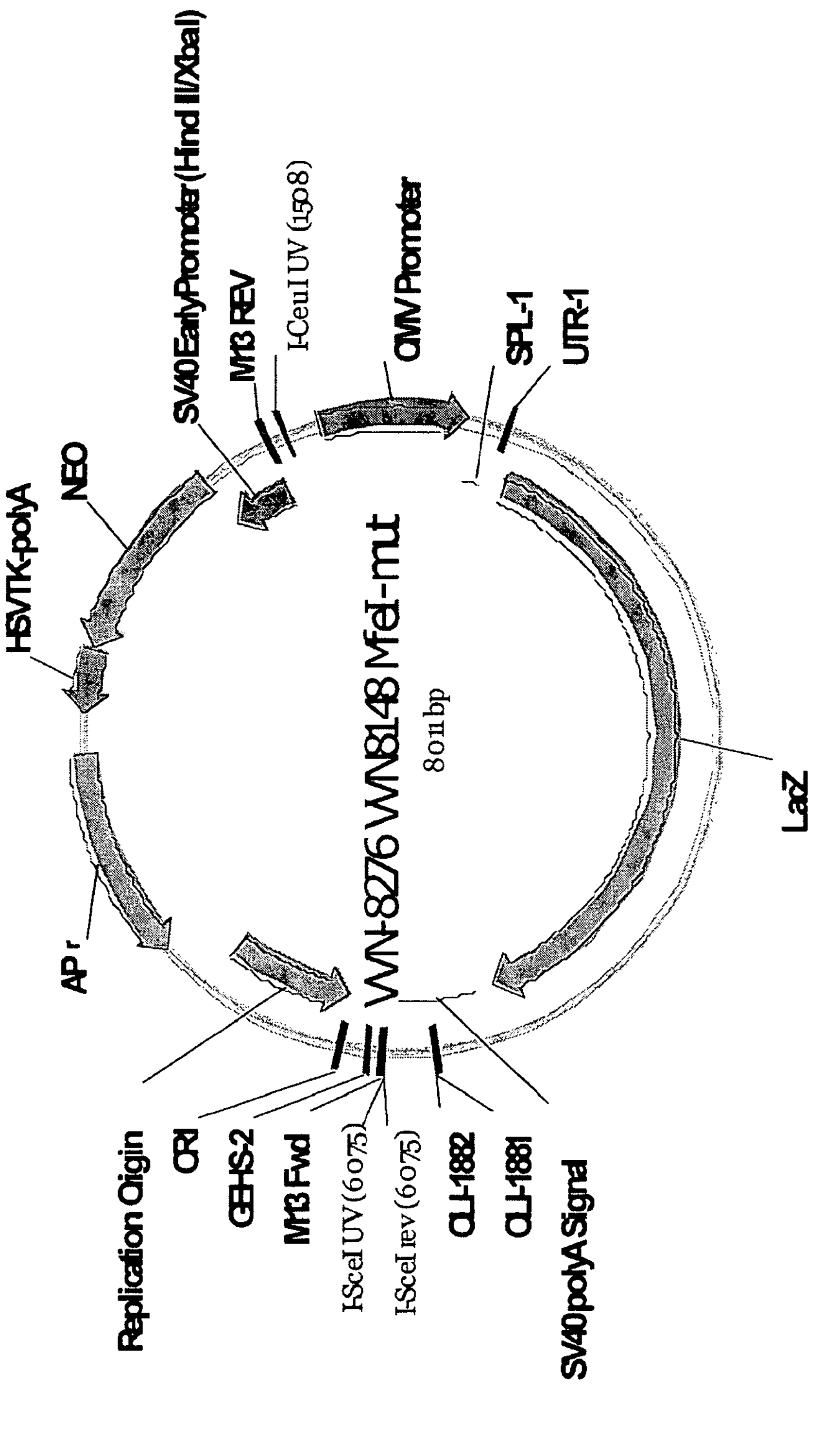
FIG. 11 depicts a vector used in Example 1 (VVN-8276), wherein beta-galactosidase (LacZ) coding sequence is operably linked to a 5'UTR of the invention (INXN-1) and the CMV promoter.

11. The sequence of the vector of FIG. 10 is provided in SEQ ID NO:12; the sequence of the vector of FIG. 11 is provided in SEQ ID NO:13.

In another embodiment, the vector is an expression vector comprising, as arranged from 5' to 3', a promoter, a chimeric polynucleotide, and a cloning site, wherein:

a. the chimeric polynucleotide comprises a polynucleotide fragment of a first eukaryotic gene comprising at least one splice site and a polynucleotide fragment of a second eukaryotic gene comprising at least a portion of 5' untranslated region; and b. the chimeric polynucleotide is positioned between the promoter and the cloning site, wherein the polynucleotide fragment of the first eukaryotic gene is positioned toward the promoter and polynucleotide fragment of the second eukaryotic gene is positioned toward the cloning site.

The cloning site of the expression vector may comprise one or more unique restriction sites so that a sequence of interest may be inserted. In another embodiment, the cloning site comprises recombinase attachment sites so that a sequence of interest may be inserted by site-specific recombination.

Figure 3B:
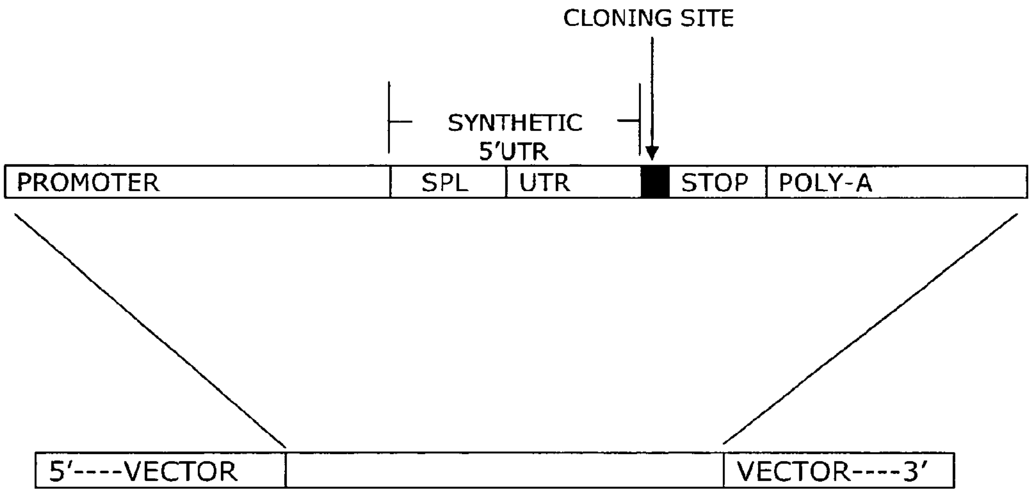
FIG. 3B depicts a schematic representation of a synthetic 5'UTR inserted into an expression vector between a promoter and a cloning site.

An embodiment of the expression vector is depicted schematically in FIG. 3B. In FIG. 3B, SPL refers to the polynucleotide fragment comprising the splice site and UTR refers to the polynucleotide fragment comprising at least a portion of 5' untranslated region. SPL and UTR together make up a synthetic 5'UTR.

The polynucleotide fragment comprising the splice site in the expression vector may be a fragment of any eukaryotic gene. Exemplary polynucleotide fragments that may be used within the expression vector include those comprising a splice site of a eukaryotic sarcoplasmic/endoplasmic reticulum calcium ATPase gene described herein. Further, the polynucleotide fragment comprising at least a portion of 5' untranslated region may be a fragment of any eukaryotic gene. Exemplary polynucleotide fragments that may be used within the expression vector include those comprising at least a portion of a 5'UTR of a casein gene described herein.

The expression vectors of the invention may further comprise one or more additional polynucleotide sequences downstream of the sequence of interest or cloning site for creating an in-frame fusion with the polypeptide encoded by the sequence of interest. For example, the additional polynucleotides downstream of the sequence of interest may encode an epitope tag, a reporter, or purification tag. Epitope tags are known in the art and include myc, hemagluttinin (HA), and FLAG. Examples of reporters include green fluorescent protein and its variants, beta-galactosidase (LacZ), beta-glucuronidase (Gus) chloramphenicol acetyltransferase (CAT) and luciferase. Examples of purification tags include $His_6$ and GST. The expression vector may also comprise a polyA site downstream of the sequence of interest or cloning site.

Depending upon the desired outcome, the promoter portion of the expression vector containing a synthetic 5'UTR can be a constitutive promoter, a non-constitutive promoter, a tissue-specific promoter (constitutive or non-constitutive), a pathogenesis or disease related promoter, a developmental specific promoter, or a selectively controlled promoter such as an inducible promoter. Different selectively controlled promoters are controlled by different mechanisms. For example, a tetracycline-inducible promoter is activated to express a downstream coding sequence when the cell containing the promoter and other necessary cellular factors is treated with tetracycline. Other inducible promoters are activated by other drugs or factors. RHEOSWITCH is an inducible promoter system available from New England Biolabs (Ipswich, Mass.). Temperature sensitive promoters can also be used to increase or decrease gene expression. An embodiment of the invention comprises a gene construct containing a synthetic 5'UTR whose expression is controlled by an inducible promoter.

The invention includes embodiments wherein the vector backbone comprising the synthetic 5'UTR comprises sequences suitable for expression of a sequence of interest in a eukaryotic cell. In one embodiment, the vector backbone comprising the synthetic 5'UTR comprises sequences suitable for expression of a sequence of interest in a cell of mammal. Mammalian expression vectors may comprise non-transcribed elements such as an origin of replication, a suitable promoter and enhancer linked to the sequence of interest to be expressed, and other 5' or 3' flanking nontranscribed sequences, and 5' or 3' nontranslated sequences, such as necessary ribosome binding sites, a poly-adenylation site, and transcriptional termination sequences. Examples of mammalian expression vectors are well known in the art and include pcDNA3 (Invitrogen) and pRSVneo (ATTC).

For example, the promoter portion of an expression vector containing a synthetic 5'UTR may be an animal or mammalian promoter. Exemplary animal or mammalian promoters include SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, beta-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo All control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell beta-actin, and the like. The promoters within the expression vector may modified by addition of enhancer or regulatory sequences and the like.

The sequence of interest portion of an expression vector containing a synthetic 5'UTR can be a sequence from any eukaryotic gene or portion thereof, or natural or non-natural coding or non-coding sequence. Non-limiting examples of coding sequences that may be used in the present invention include sequences encoding reporters (e.g. luciferase, beta-galactosidase, fluorescent proteins), epitopes, experimental polypeptides, or therapeutic polypeptides. Additional examples of nucleic acid sequences of interest include RNA molecules, such as small RNAs, micro RNAs, ribosomal RNAs, therapeutic RNAs, and ribozymes.

In another aspect of the invention, multiple, nonredundant synthetic 5'UTRs are used in the context of multigenic gene constructs within a single vector.

In another embodiment, the vector is a gene therapy vector comprising a synthetic gene construct comprising a synthetic 5'UTR. The gene therapy vector may be any gene therapy vector known in the art, including non-viral vectors or viral vectors such as an adenoviral vector, an adeno-associated viral (AAV) vector, or a retroviral vector. The synthetic gene construct may comprise a promoter flanking on the 5' end of the synthetic 5'UTR and a therapeutic gene of interest flanking on the 3' end of the synthetic 5'UTR as shown in FIG. 3A. The promoter may be constitutive promoter, a tissue-specific promoter, and inducible promoter, or other promoter described herein. Examples of classes of therapeutic genes of interest that may be including in the gene therapy vector include without limitation, genes encoding for cytokines, chemokines, hormones, antibodies, engineered immunoglobulin-like molecules, single chain antibodies, fusion proteins, enzymes, immune co-stimulatory molecules, immunomodulatory molecules, transdominant negative mutants of target proteins, toxins, conditional toxins, chemotherapy or radiotherapy sensitizers, antigens, tumor suppressor proteins, growth factors, membrane proteins, vasoactive proteins and peptides, anti-viral proteins or variants thereof.

Specific example of therapeutic genes of interest are myriad, and include, without limitation, erythropoietin, insulin, VEGF, FGF, Factor VIII, Factor IX, endostatin, angiostatin, GDNF, BDNF, NGF, EGF, CFTR, PEGF, IFN-alpha, IFN-gamma, IL-1, IL-2, IL-4, IL-6, IL-7, IL-10, IL-12, IL-21, GM-CSF, G-CSF, M-CSF, TNF-α, TNF-β, TGF-α, TGF-β, CD40, hirudin, and the like.

The present invention also provides kits comprising the polynucleotide sequences of the invention. For example, in one embodiment, the present invention provides a kit comprising at least one polynucleotide that is at least 80%, 85%, 90%, 95%, 96%, 97%, 98% or 99% identical to a polynucleotide that is represented by one of SEQ ID NOS:1-10. The kits may comprise the above vectors or components that permit their assembly. For example, the kit may include a vector that may be linearized through digestion with a restriction enzyme at a site that permits the user to insert a synthetic 5'UTR or individual components of a synthetic 5'UTR. The kit may further comprise additional components for assembly of the vector, such as the restriction enzyme, ligase, buffer, and the like.

The present invention further provides methods for expressing a gene product or a sequence of interest in a host cell.

For example, another embodiment of the invention is a method of expressing a gene product comprising transfecting a host cell with a synthetic gene construct comprising a synthetic 5'UTR described herein.

Another embodiment of the invention is a method of expressing a gene product comprising transfecting a host cell with a synthetic gene construct comprising a polynucleotide at least 80%, 85%, 90%, 95%, 96%, 97%, 98% or 99% identical to a polynucleotide represented by SEQ ID NO:1 or SEQ ID NO:7.

Another embodiment of the invention is a method for expressing a sequence of interest in a host cell, comprising the steps of:

a. transfecting a host cell with an expression vector comprising a synthetic gene construct described herein; and
b. culturing said host cell under conditions suitable to obtain expression of said sequence of interest.

In another method for expressing a sequence of interest in a host cell, a sequence of interest may be inserted into an expression vector described herein comprising a promoter, a synthetic 5'UTR, and a cloning site. For example, another embodiment of the invention is a method for expressing a sequence of interest in a host cell, comprising the steps of:

a. inserting a sequence of interest to be expressed within an expression vector described herein comprising a promoter, a synthetic 5'UTR, and a cloning site at the cloning site, wherein the sequence of interest to be expressed includes an RNA or a polypeptide coding sequence;
b. transfecting a host cell with the expression vector; and
c. culturing said host cell under conditions suitable to obtain expression of said sequence of interest.

In another method for expressing a sequence of interest in a host cell, a synthetic 5'UTR may be inserted into the expression vector between the promoter and the sequence of interest, such that the portion comprising the splice element of a eukaryotic gene within the synthetic 5'UTR is positioned toward the promoter and the portion comprising at least a portion of a 5'UTR of another eukaryotic gene is positioned toward the sequence of interest.

For example, another embodiment of the invention is a method for expressing a sequence of interest in a host cell, comprising the steps of:

a. inserting a synthetic 5'UTR described herein into an expression vector between a promoter and a sequence of interest to be expressed, wherein the sequence of interest to be expressed includes an RNA or a polypeptide coding sequence;
b. transfecting a host cell with said expression vector; and
c. culturing said host cell under conditions suitable to obtain expression of said sequence of interest.

Another embodiment of the invention is a method for expressing a sequence of interest in a host cell, comprising the steps of:

a. inserting a polynucleotide at least 80%, 85%, 90%, 95%, 96%, 97%, 98% or 99% to a polynucleotide represented by SEQ ID NO:1 or SEQ ID NO:7 into an expression vector between a promoter and a sequence of interest to be expressed, wherein the sequence of interest to be expressed includes an RNA or a polypeptide coding sequence;
b. transfecting a host cell with said expression vector; and
c. culturing said host cell under conditions suitable to obtain expression of said sequence of interest.

The methods of the invention are carried out using routine techniques. Unless otherwise stated, recombinant DNA techniques are performed according to standard protocols described in (Sambrook, supra) or in Volumes 1 and 2 of Ausubel et al. (1994), Current Protocols in Molecular Biology, Current Protocols.

The present invention also provides host cells comprising a synthetic 5'UTR. The host cells are contemplated to include any of the embodiments of the synthetic 5'UTR polynucleotide sequences described herein. For example, another embodiment of the invention is a host cell comprising a synthetic 5'UTR polynucleotide sequence comprising a polynucleotide fragment comprising the second intron of a eukaryotic sarcoplasmic/endoplasmic reticulum calcium ATPase gene fused to a polynucleotide fragment comprising at least a portion of the 5'UTR region of a casein gene.

In one embodiment, the host cell is a mammalian host cell. In specific embodiments, the host cell is a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Specific examples of host cells of the invention comprising a synthetic 5'UTR include, but are not limited to A549, ARPE-19, CH3/10T1/2, C2C12, aco2, COS7, FL-83B, HEK-293, HEPG2, HeLa, HT-1080, MDCK, P19, SH-SY5Y, Sol 8, and U87.

The host cells of the invention are transfected with a polynucleotide comprising a synthetic 5'UTR. Host cell transfection is well known in the art and may be achieved by a variety of methods including but not limited to electroporation, viral infection, plasmid/vector transfection, non-viral vector mediated transfection, particle bombardment, and the like. Expression of desired gene products involves culturing the transfected host cells under suitable conditions and measuring expression of the transfected gene. Culture conditions and gene expression protocols in eukaryotic cells are well known in the art.

The present invention also provides host organisms comprising a synthetic 5'UTR described herein. The synthetic 5'UTRs may be inserted directly into the genome of a host organism in vivo. For example, in one embodiment, a synthetic 5'UTR is introduced into a host organism to replace a wild-type 5'UTR by directly introducing into the host organisms a vector that contains a synthetic 5'UTR of the invention flanked by sequences homologous to sequences flanking the wild-type 5'UTR that is to be replaced. In another embodiment, a synthetic gene construct comprising a synthetic 5'UTR is inserted into the genome of a host organism by introducing an integrating vector comprising the gene construct into the host organism. Tissue-specificity of the insertion can be controlled, for example, by the route of vector administration. In another embodiment, a synthetic gene construct comprising a synthetic 5'UTR is introduced into a host organism by introducing a non-integrating vector comprising the gene construct into the host organism.

A synthetic 5'UTR or a synthetic gene construct comprising a synthetic 5'UTR may also be introduced into a host organism through ex vivo approaches. For example, autologous or non-autologous cells can be transformed with a vector comprising a synthetic 5'UTR and then introduced into the host organism.

In another embodiment, a synthetic 5'UTR is introduced into the genome of a host cell or organism using a site-specific recombinase system such as the Cre/loxP system. In this embodiment, stable integration of a DNA fragment such as a fragment comprising a synthetic 5'UTR or a synthetic gene construct comprising a synthetic 5'UTR into the genome is achieved by introducing modified lox sites into the genome and the donor vector that prevent re-excision of the integrated DNA (see Metzger and Feil, Current Opinion in Biotechnology, 10:470-476 (1999), incorporated by reference herein). Further, heterospecific loxP sites can be introduced ('floxed') into the genome to flank a region to be replaced (Metzger and Feil, supra), such as an endogenous 5'UTR and a synthetic 5'UTR on a donor plasmid. Transgenic animals with lox P chromosomal sites introduced in the genome may be crossed with transgenic mice expressing Cre recombinase driven by a tissue or cell-specific promoter, which are known in the art. Administration of a donor plasmid comprising a synthetic 5'UTR to progeny of this crossing will result in integration within specific tissues or cell types.

In other embodiments, other site-specific recombination systems such as those disclosed in United States Patent Application Publication No. 20060172377, incorporated by reference herein, are used to introduce a synthetic 5'UTR into the genome of a host organism.

Another embodiment of the invention is a non-human organism comprising a polynucleotide at least 80%, 85%, 90%, 95%, 96%, 97%, 98% or 99% identical to a polynucleotide represented by SEQ ID NOS:1-10.

Another embodiment of the invention is a non-human organism comprising a synthetic gene construct comprising a polynucleotide at least 80%, 85%, 90%, 95%, 96%, 97%, 98% or 99% identical to a polynucleotide represented by SEQ ID NOS:1-10.

Further, a transgenic organism such as a mouse comprising a synthetic 5'UTR or a gene construct comprising a synthetic 5'UTR may be created. For example, transgenic mice can be generated by injected an appropriate vector comprising the synthetic 5'UTR into the pronuclei of fertilized mouse oocytes. Alternatively, the vector can be introduced into mouse embryonic stem cells, which are then microinjected into mouse blastocysts. The transformed zygotes or blastocyts are then transplanted into pseudopregnant female mice. The resultant pups are screened for the presence of the polynucleotides by PCR or Southern blotting. Heterozygous transgenic animals are then crossed with each other to generate homozygotes. In one embodiment, the synthetic 5'UTR replaces an endogenous 5'UTR of a gene of interest in the transgenic animal through homologous recombination.

Thus, another embodiment of the invention is a transgenic animal comprising a synthetic 5'UTR polynucleotide sequence comprising a fragment of a eukaryotic sarcoplasmic/endoplasmic reticulum calcium ATPase gene comprising the second intron fused to a fragment comprising at least a portion of the 5'UTR of a casein gene.

Another embodiment of the invention is a transgenic organism comprising a polynucleotide at least 80%, 85%, 90%, 95%, 96%, 97%, 98% or 99% identical to a polynucleotide represented by SEQ ID NOS:1-10.

Another embodiment of the invention is a transgenic organism comprising a synthetic gene construct comprising a polynucleotide at least 80%, 85%, 90%, 95%, 96%, 97%, 98% or 99% identical to a polynucleotide represented by SEQ ID NOS:1-10.

The following examples are illustrative, but not limiting, of embodiments of the present invention. Other suitable modifications and adaptations which are obvious to those skilled in the art are within the spirit and scope of the invention.

EXAMPLES

Example 1

Figure 9:
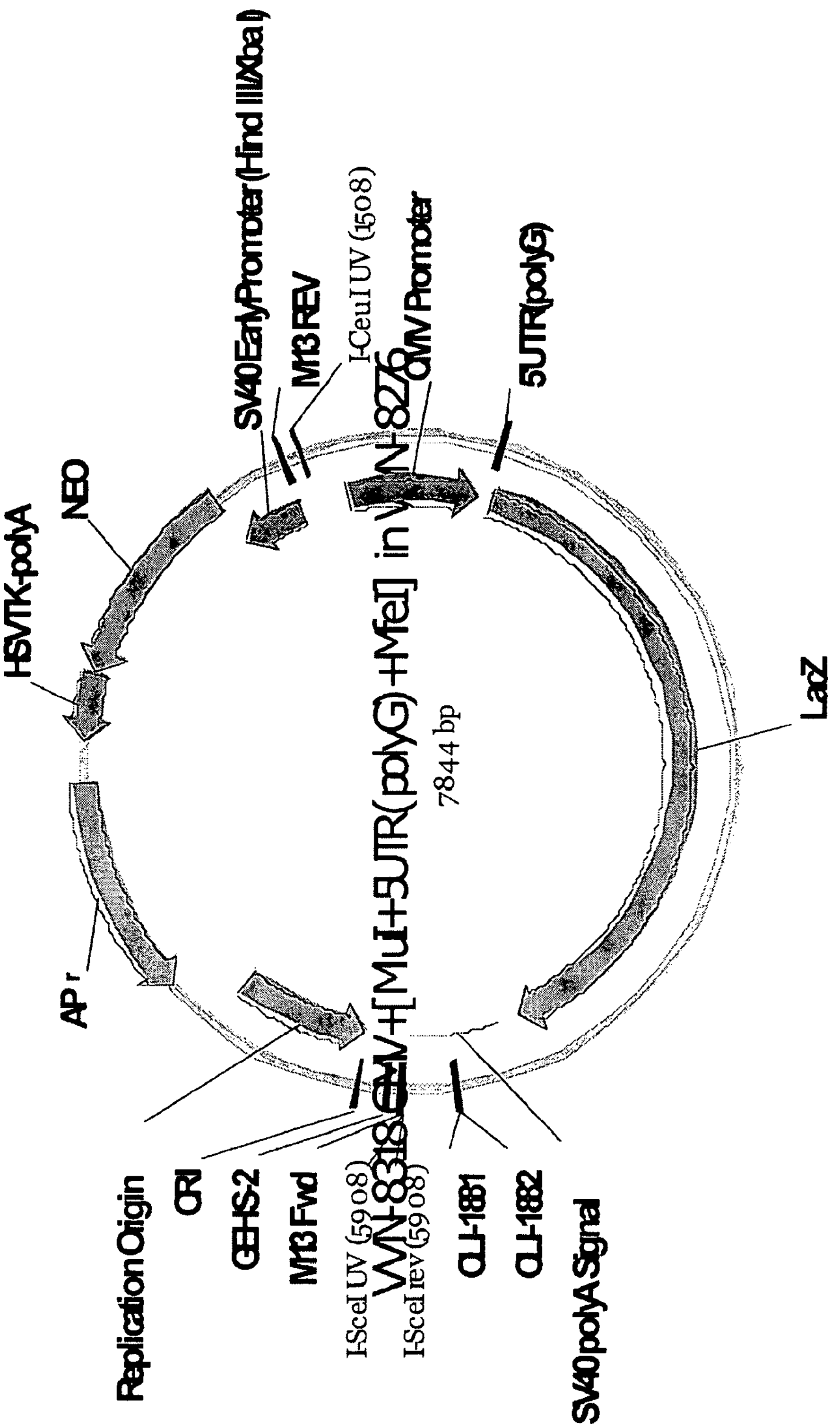
FIG. 9 depicts a vector used in Example 1 (VVN-8318), wherein beta-galactosidase (LacZ) coding sequence is operably linked to polyG 5'UTR and the CMV promoter.

Three different versions of a synthetic 5'UTR were constructed, and inserted into a vector wherein a human cytomegalovirus (CMV) promoter directs expression of a beta-galactosidase reporter (LacZ coding sequence). In version one, polyG (12) was inserted between the promoter and the beta-galactosidase reporter as a synthetic 5'UTR (FIG. 9). In version two, called 5U2, SEQ ID NO:1 was inserted between the promoter and the beta-galactosidase reporter as a synthetic 5'UTR (FIG. 10). In version 3, called INXN-1, SEQ ID NO:7 was inserted between the promoter and the beta-galactosidase reporter as a synthetic 5'UTR (FIG. 11). Each transgene has an SV40 polyadenylation sequence in the 3' regulatory region. A generic version of each vector containing a 5U2 or INXN-1 synthetic 5'UTR is shown schematically in FIG. 3A. HEK-293 cells and 1080 cells were transiently transfected with each expression vector.

Beta-galactosidase was measured from the cells using the Galacto-Star™ System from Applied Biosystems (Cat Nos. BM100S, BM300S, BM2500S, BY100S, BY300S, BY2500S) according to the following protocol. Cells were lysed in 50 μL lysis solution (Galacto-Star™ System) for 10 minutes at room temperature. 100 μL of Galacton-Star® substrate was aliquoted into wells of a white opaque 96-well microplate. 10 μL of cell lysis added to 100 μL of Galacton-Star® substrate and incubated for 30 minutes. Light signal was measured using a microplate luminometer.

Figure 4:
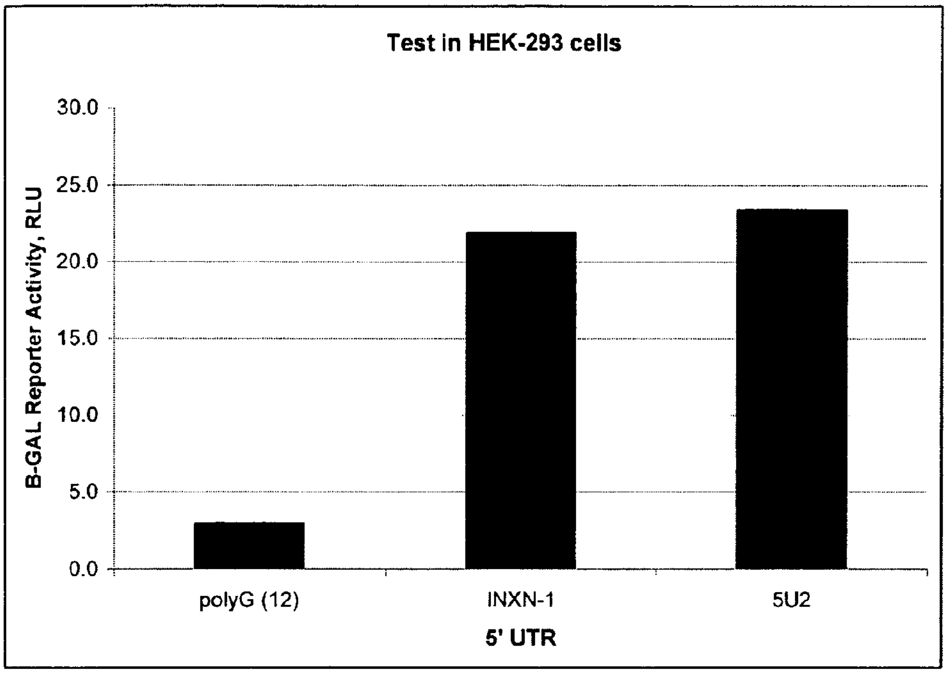
FIG. 4 depicts results of testing synthetic 5'UTR embodiments of the invention in HEK-293 cells.
Figure 5:
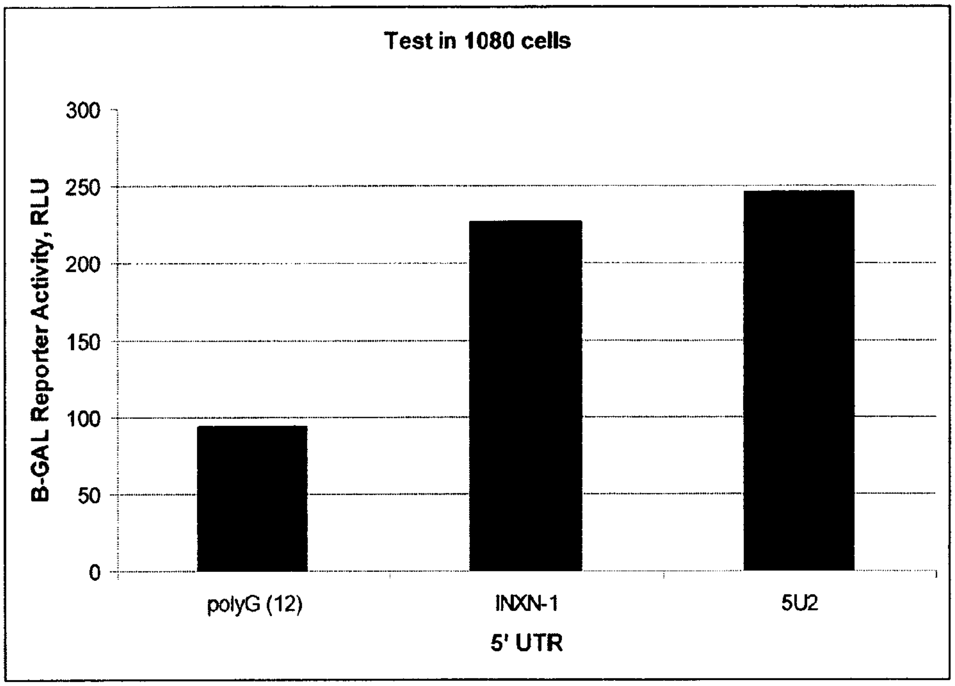
FIG. 5 depicts results of testing synthetic 5'UTR embodiments of the invention in 1080 cells.
Figure 6:
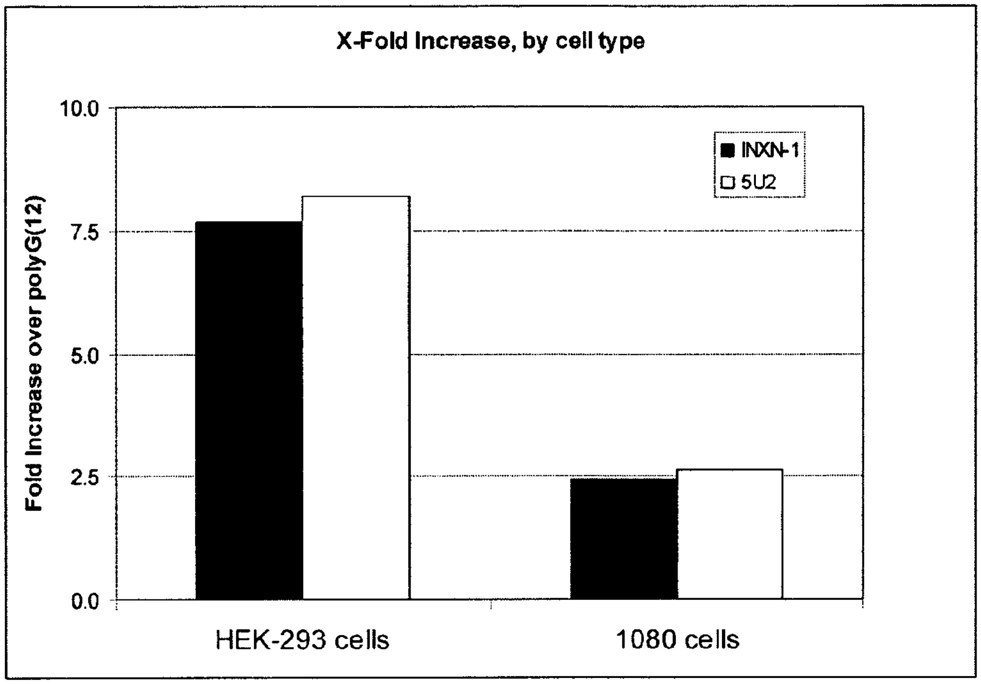
FIG. 6 depicts results of testing synthetic 5'UTR embodiments of the invention as the fold increase over control in HEK-293 cells and 1080 cells, wherein control values were normalized to 1.
Figure 7:
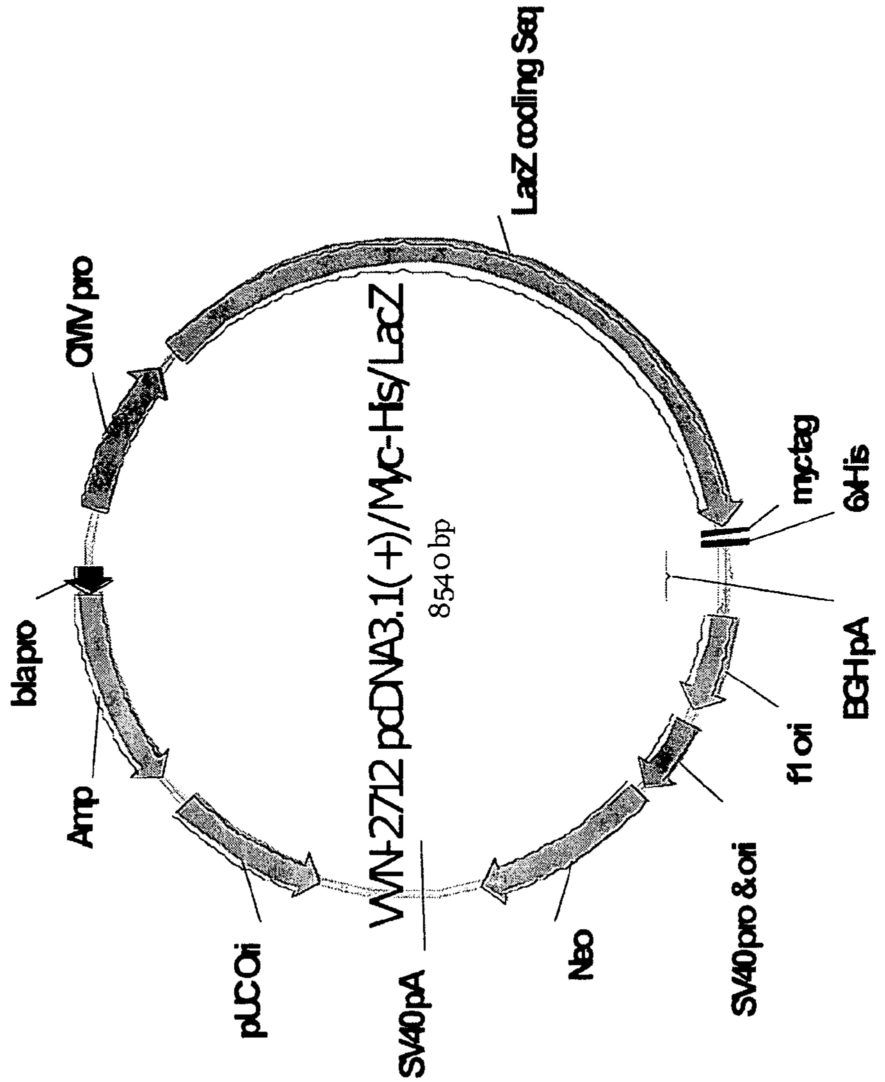
FIG. 7 depicts a control vector used in Example 1 (VVN-2712), wherein beta-galactosidase (LacZ) coding sequence lacks a 5'UTR and is operably linked to the CMV promoter.
Figure 8:
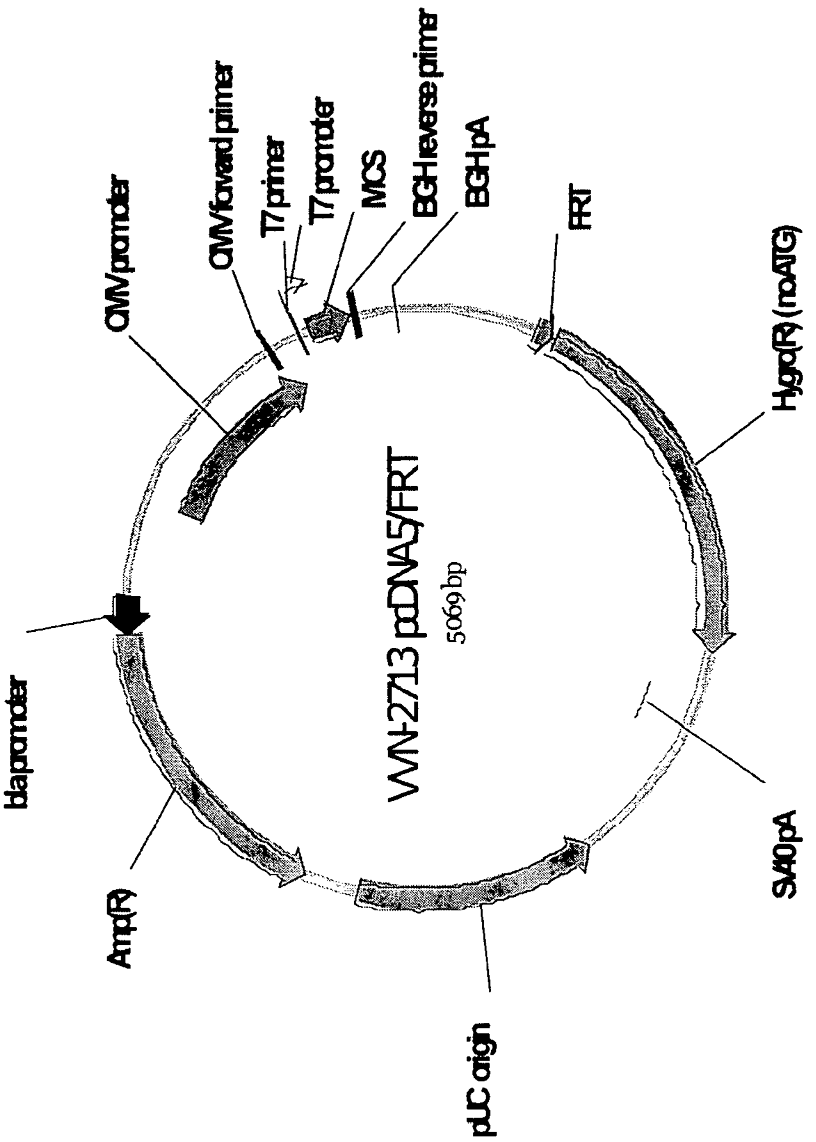
FIG. 8 depicts a control vector used in Example 1 (VVN-2713), wherein the vector lacks a 5'UTR and LacZ.

The results from HEK-293 cells are shown in FIG. 4. Beta-galactosidase reporter expression was markedly increased in HEK-293 cells transfected with vectors containing the INXN-1 or 5U2 synthetic 5'UTR in comparison to vectors containing polyG as the synthetic 5'UTR. Increased reporter expression in 1080 cells transfected with vectors containing INXN-1 or 5U2 in comparison to vectors containing polyG as the 5'UTR is shown in FIG. 5. Expression level of transgenes in vectors containing a polyG 5'UTR was similar to a control where no 5'UTR was present (VVN-2712, FIG. 7, data in FIG. 12). The negative control to measure assay background was a vector with no beta-galactosidase (VVN-2713, FIG. 8, data in FIG. 12). FIG. 6 shows that the synthetic beta-galactosidase reporter gene containing the INXN-1 synthetic 5'UTR was expressed about 7.5 times higher in HEK-293 cells and about 2.5 times higher in 1080 cells in comparison to a synthetic reporter gene containing polyG as the 5'UTR, while a synthetic reporter gene containing the 5U2 synthetic 5'UTR was expressed about 8 times higher in HEK-293 cells and about 2.5 times higher in 1080 cells in comparison to the synthetic reporter gene containing polyG as the 5'UTR.

Example 2

A search of the GenBank non-redundant, nucleotide public database using the blastn algorithm with default parameters, using SEQ ID NO:4 as the query sequence yielded the following representative SERCA2 homologues listed in Table 1. SEQ ID NO:4 represents a component of the synthetic 5'UTR represented by SEQ ID NO:7.

TABLE 1

| Accession Number | Description | Query Coverage | E value | Maximum Identity |
|---|---|---|---|---|
| EU365364 | *Homo sapiens* ATPase CA++ transporting cardiac muscle slow twitch 2 (ATP2A2) gene, exons 2,3 and partial cds. | 99% | 2e−16 | 77% |
| AM137440 | *Equus caballus* atp2A2 gene for sarcoplasmic/endoplasmic reticulum calcium ATPase 2, exons 1-20. | 51% | 3e−14 | 90% |
| M33834 | *Oryctolagus cuniculus* sarco(endo)plasmic reticulum Ca-2+-ATPase (SERAC2) gene, exons 1-3 and partial cds. | 53% | 5e−05 | 80% |

A fragment of the *Equus caballusa* genome identified from the BLAST search results in Table 1 (public accession number AM137440) was compared to the *Equus caballusa* SERCA2 mRNA sequence NM_001081765 using the pairwise alignment function in the publicly available program DNA Strider 1.4f17 (see Marck, C, Nucleic Acids Research 16(5):1829-1837 (1988) and Douglas, S, Molecular Biotechnology 3(1):37-45 (1995) for descriptions of DNA Strider). The sequences were aligned using the Blocks method using default parameters for mismatch penalty and gap penalty. A portion of the alignment of the *Equus caballusa* genomic (SEQ ID NO: 16) and mRNA sequence (SEQ ID NO: 15) is shown in FIG. 13, with arrows marking the beginning and end of the second intron of the *Equus caballusa* SERCA2 gene. The region of homology that is 5' to the intron represents exon 2, and the region of homology that is 3' to the intron represents exon 3.

An oligonucleotide representing a fragment of the *Equus caballusa* SERCA2 gene comprising the second intron is then synthesized and fused to SEQ ID NO:3 using recombinant DNA techniques to create a synthetic 5'UTR. The synthetic 5'UTR is then inserted into a vector between a human cytomegalovirus promoter (CMV) and a luciferase reporter gene. The vector and a control vector with a polyG 5'UTR are then used to transfect 3T3 cells. Luciferase activity is measured using a luminometer and relative light units are compared between both sets of cells. Expression of reporter in cells transfected with the vector containing the synthetic 5'UTR is elevated compared to cells transfected with the vector containing the polyG 5'UTR.

Example 3

A search of the GenBank non-redundant, nucleotide public database using the blastn algorithm with default parameters, using SEQ ID NO:3 as the query sequence yielded the following representative homologues listed in Table 2. SEQ ID NO:3 represents the bovine casein 5'UTR component of the synthetic 5'UTR represented by SEQ ID NO:1 and SEQ ID NO:7.

TABLE 2

| Accession Number | Description | Query Coverage | E value | Maximum Identity |
|---|---|---|---|---|
| DQ317447 | *Bubalus bubalis* beta-casein mRNA, complete cds | 77% | 5e−10 | 97% |
| NM_001009373 | *Ovis aries* casein beta (CSN2), mRNA. | 77% | 6e−09 | 95% |
| AY311384 | *Capra hircus* beta-casein gene, promoter and exon 1. | 56% | 5e−04 | 96% |
| NM_001081852 | *Equus caballus* casein beta (CSN2), mRNA. | 58% | 0.002 | 93% |
| AY452035 | *Sus scrofa* beta casein gene, promoter region, exon 1, and partia sequence. | 56% | 0.006 | 93% |
| AJ409279 | *Camelus dromedarius* partial gene for beta-casein, 5' flanking region. | 56% | 0.006 | 93% |
| NM_001082759 | *Oryctolagus cuniculus* pre-beta-casein (AA −15 to 213) (LOC100009539), mRNA. | 66% | 0.006 | 88% |
| NM_001003086 | *Canis lupus familiaris* casein beta (CSN2), mRNA. | 67% | 0.88 | 83% |

The second intron of each representative SERCA2 gene listed in Table 1 is identified using a pairwise alignment program alignment program by comparing the genomic sequence with its respective mRNA sequence. A first set of oligonucleotides is synthesized comprising the second intron of SERCA2 for each SERCA2 homologue. A second set of oligonucleotides is then synthesized representing at least a portion of 5'UTR for each beta-casein homologue identified in Table 2. The portion of 5'UTR comprises the portion of query coverage identified in the BLAST results of Table 2. A set of synthetic 5'UTRs is then constructed using recombinant DNA techniques by fusing a unique member of the first set of oligonucleotides comprising the second intron of SERCA2, or an oligonucleotide represented by SEQ ID NOS:2 and 4-6 to a unique member of the second set of oligonucleotides comprising at least a portion of 5'UTR or an oligonucleotide represented by SEQ ID NOS:3 and 8-10 wherein the oligonucleotide comprising the second intron of SERCA2 is fused 5' of the oligonucleotide comprising the portion of 5'UTR. Restriction sites are then added to each end of the synthetic 5'UTR through PCR. Each unique synthetic 5'UTR is then inserted within a vector between a human CMV promoter and a lacZ promoter. 1080 cells in 96 well plates are then transfected with each vector as well as a control vector with a polyG 5'UTR. Beta-galactosidase activity is then measured using the assay described in Example 1 and levels of expression relative to the polyG 5'UTR are then compared.

Having now fully described the invention, it will be understood by those of ordinary skill in the art that the same can be performed within a wide and equivalent range of conditions and other parameters without affecting the scope of the invention or any embodiment thereof.

What is claimed is:

1. A polynucleotide construct comprising: a first polynucleotide comprising one of SEQ ID NOS:2 and 4-6, a second polynucleotide comprising one of SEQ ID NOS:3 and 8-10, a third polynucleotide encoding a sequence of interest to be expressed in a cell, wherein the first polynucleotide is located 5' of the second polynucleotide.

2. The polynucleotide construct of claim 1, wherein the polynucleotide construct lacks restriction sites for the following restriction endonucleases: AsiS I, Pac I, SbfI, Fse I, Asc I, MIu I, SnaB I, Not I, Sal I, Swa I, Rsr II, BsiW I, Mfe I, Nhe I, Nsi I, CIa I, Nde I, Nsi I, Kpn I, Nco I and Pst I.

3. The polynucleotide construct of claim 1, wherein the polynucleotide construct includes restriction sites at the 5' and 3' ends to facilitate cloning into a vector.

4. The polynucleotide construct of claim 3, wherein the polynucleotide includes a restriction site for MIu I at the 5' end and a restriction site for Mfe I at the 3' end.

5. A vector comprising the polynucleotide construct of claim 1.

6. A synthetic gene construct comprising the polynucleotide construct of claim 1.

7. A host cell comprising the polynucleotide construct of claim 1.

8. A kit comprising the polynucleotide construct of claim 1.

9. An expression vector comprising a promoter and the polynucleotide construct of claim 1, wherein the polynucleotide construct is operably linked to the promoter, and positioned between a promoter and the sequence of interest to be expressed, wherein the first polynucleotide is positioned toward the promoter, and wherein the second third polynucleotide is positioned 3' of the second polynucleotide.

10. A method for expressing the sequence of interest in a host cell, the method comprising:

(a) transfecting a host cell with the expression vector of claim 9; and (b) culturing said host cell under conditions suitable to obtain expression of said sequence of interest.

11. The polynucleotide construct of claim 1, wherein the first polynucleotide comprises SEQ ID NO:2 and the second polynucleotide comprises SEQ ID NO:3.

12. The polynucleotide construct of claim 1, wherein the first polynucleotide comprises SEQ ID NO:4 and the second polynucleotide comprises SEQ ID NO:3.

13. The polynucleotide construct of claim 1, wherein the polynucleotide construct comprises SEQ ID NO:1 or SEQ ID NO:7.

* * * * *

UNITED STATES PATENT AND TRADEMARK OFFICE

CERTIFICATE OF CORRECTION

PATENT NO. : 8,835,621 B2
APPLICATION NO. : 12/681609
DATED : September 16, 2014
INVENTOR(S) : Reed It is certified that error appears in the above-identified patent and that said Letters Patent is hereby corrected as shown below:

In the Claims

Claim 2, column 55, line 19, please change "SbfI" to "Sbf I".

Claim 9, column 56, please delete lines 14-16 "and positioned between a promoter and the sequence of interest to be expressed, wherein the first polynucleotide is positioned toward the promoter, and".

line 17, delete "second".

Signed and Sealed this
Second Day of December, 2014

Michelle K. Lee
*Deputy Director of the United States Patent and Trademark Office*

```
                            SEQUENCE LISTING

<160> NUMBER OF SEQ ID NOS: 16

<210> SEQ ID NO 1
<211> LENGTH: 191
<212> TYPE: DNA
<213> ORGANISM: Artificial
<220> FEATURE:
<223> OTHER INFORMATION: synthetic

<400> SEQUENCE: 1

acgcgtcgaa gaaggtgagt aatcttaaca tgctcttttt tttttttttt gctaatccct      60

tttgtgtgct gatgttagga tgacatttac aacaaatgtt tgttcctgac aggaaaaacc    120

ttgctgggta ccttcgttgc cggacacttc ttgtcctcta ctttggaaaa aaggaattga    180

gagcccaatt g                                                         191

<210> SEQ ID NO 2
<211> LENGTH: 120
<212> TYPE: DNA
<213> ORGANISM: Artificial
<220> FEATURE:
<223> OTHER INFORMATION: synthetic

<400> SEQUENCE: 2

cgaagaaggt gagtaatctt aacatgctct tttttttttt ttttgctaat cccttttgtg     60

tgctgatgtt aggatgacat ttacaacaaa tgtttgttcc tgacaggaaa aaccttgctg    120

<210> SEQ ID NO 3
<211> LENGTH: 53
<212> TYPE: DNA
<213> ORGANISM: Artificial
<220> FEATURE:
<223> OTHER INFORMATION: synthetic

<400> SEQUENCE: 3

ttcgttgccg gacacttctt gtcctctact ttggaaaaaa ggaattgaga gcc            53

<210> SEQ ID NO 4
<211> LENGTH: 120
<212> TYPE: DNA
<213> ORGANISM: Artificial
<220> FEATURE:
<223> OTHER INFORMATION: synthetic

<400> SEQUENCE: 4

cgaagaaggt gagtaatctt aacatgttct tttttttttt tttttttaat cccttttgtg     60

tgctgatgtt aggatgacat ttacaacaaa tgtttgttcc tgacaggaaa aaccttgctg    120

<210> SEQ ID NO 5
<211> LENGTH: 192
<212> TYPE: DNA
<213> ORGANISM: Artificial
<220> FEATURE:
<223> OTHER INFORMATION: synthetic

<400> SEQUENCE: 5
```

-continued

```
agttaccggc tgaagaaggt aatcttaaca tgctgtttct gtttttttc ctctgttggt     60

gtgctgatgg taagatgaca gttaaaacac atgtgtttgt ttcttacagg aaaaaccttg    120

ctggaacttg tgattgagca gtttgaagac ttgctagtta ggattttatt actggcagca    180

tgtatatctt tt                                                        192


<210> SEQ ID NO 6
<211> LENGTH: 218
<212> TYPE: DNA
<213> ORGANISM: Artificial
<220> FEATURE:
<223> OTHER INFORMATION: synthetic

<400> SEQUENCE: 6

aattgccggc tgaagaaggt aaataatatt aacatgttat tttggagaga tgatgtgtgc     60

aggctgattg atgtggacaa ttgaaacaaa tggtttgttt ttttttttt tttttttcct    120

ttccttttct aacaggaaaa accttgctgg aacttgtgat tgagcagttt gaagacttac    180

tagttagaat tttactgctg gcagcatgta tatctttc                           218


<210> SEQ ID NO 7
<211> LENGTH: 199
<212> TYPE: DNA
<213> ORGANISM: Artificial
<220> FEATURE:
<223> OTHER INFORMATION: synthetic

<400> SEQUENCE: 7

ggcgcgccac gcgtcgaaga aggtgagtaa tcttaacatg ctcttttttt tttttttttt     60

taatcccttt tgtgtgctga tgttaggatg acatttacaa caaatgtttg ttcctgacag    120

gaaaaacctt gctgggtacc ttcgttgccg gacacttctt gtcctctact ttggaaaaaa    180

ggaattgaga gcccaattg                                                 199


<210> SEQ ID NO 8
<211> LENGTH: 43
<212> TYPE: DNA
<213> ORGANISM: Artificial
<220> FEATURE:
<223> OTHER INFORMATION: synthetic

<400> SEQUENCE: 8

gcttcacctc ctctcttgtc ctccactaaa ggacttgaca gcc                       43


<210> SEQ ID NO 9
<211> LENGTH: 52
<212> TYPE: DNA
<213> ORGANISM: Artificial
<220> FEATURE:
<223> OTHER INFORMATION: synthetic

<400> SEQUENCE: 9

atcctctgag cttcatcttc tctcttgtcc tccgctaaag gacttgacag cc             52


<210> SEQ ID NO 10
<211> LENGTH: 60
<212> TYPE: DNA
<213> ORGANISM: Artificial
<220> FEATURE:
<223> OTHER INFORMATION: synthetic

<400> SEQUENCE: 10

atccattcag cttctccttc acttcttctc ctctactttg gaaaaaagga atcgagagcc     60
```

<210> SEQ ID NO 11
<211> LENGTH: 83
<212> TYPE: DNA
<213> ORGANISM: Artificial
<220> FEATURE:
<223> OTHER INFORMATION: synthetic

<400> SEQUENCE: 11
gaaaaacctt gctggaactt gtgatcgagc agtttgaaga cttactagtt cgaatattat 60
tgctggcagc gtgtatatct ttt 83

<210> SEQ ID NO 12
<211> LENGTH: 8011
<212> TYPE: DNA
<213> ORGANISM: Artificial
<220> FEATURE:
<223> OTHER INFORMATION: synthetic

<400> SEQUENCE: 12
taaacaaata ggggttccgc gcacatttcc ccgaaaagtg ccacctgacg tcacctggtc 60
ttaagggcta tggcagggcc tgccgccccg acgttggctg cgagccctgg gccttcaccc 120
gaacttgggg ggtggggtgg ggaaaaggaa gaaacgcggg cgtattggcc ccaatggggt 180
ctcggtgggg tatcgacaga gtgccagccc tgggaccgaa ccccgcgttt atgaacaaac 240
gacccaacac cgtgcgtttt attctgtctt tttattgccg tcatagcgcg ggttccttcc 300
ggtattgtct ccttccgtgt ttcactcgag tcagaagaac tcgtcaagaa ggcgatagaa 360
ggcgatgcgc tgcgaatcgg gagcggcgat accgtaaagc acgaggaagc ggtcagccca 420
ttcgccgcca agctcttcag caatatcacg ggtagccaac gctatgtcct gatagcggtc 480
cgccacaccc agccggccac agtcgatgaa tccagaaaag cggccatttt ccaccatgat 540
attcggcaag caggcatcgc catgggtcac gacgagatcc tcgccgtcgg gcatgcgcgc 600
cttgagcctg gcgaacagtt cggctggcgc gagcccctga tgctcttcgt ccagatcatc 660
ctgatcgaca agaccggctt ccatccgagt acgtgctcgc tcgatgcgat gtttcgcttg 720
gtggtcgaat gggcaggtag ccggatcaag cgtatgcagc cgccgcattg catcagccat 780
gatggatact ttctcggcag gagcaaggtg agatgacagg agatcctgcc ccggcacttc 840
gcccaatagc agccagtccc ttcccgcttc agtgacaacg tcgagcacag ctgcgcaagg 900
aacgcccgtc gtggccagcc acgatagccg cgctgcctcg tcctgcagtt cattcagggc 960
accggacagg tcggtcttga caaaaagaac cgggcgcccc tgcgctgaca gccggaacac 1020
ggcggcatca gagcagccga ttgtctgttg tgcccagtca tagccgaata gcctctccac 1080
ccaagcggcc ggagaacctg cgtgcaatcc atcttgttca atggccgatc ccatggtggc 1140
tctagaggaa tagctcagag gccgaggcgg cttcggcctc tgcataaata aaaaaaatta 1200
gtcagccatg gggcggagaa tgggcggaac tgggcggagt taggggcggg atgggcggag 1260
ttaggggcgg gactatggtt gctgactaat tgagatgcat gctttgcata cttctgcctg 1320
ctggggagcc tggggacttt ccacacctgg ttgctgacta attgagatgc atgctttgca 1380
tacttctgcc tgctggggag cctggggact ttccacaccc taacaagctt gcccgggcag 1440
cggataacaa tttcacacag gaaacagcta tgaccatgat tagctgagct aactataacg 1500
gtcctaaggt agcgaatcga tgcgatcgct taattaacct gcagggatat cccatggggg 1560
ccgcgagctc tcccccgggg gaacagcatg cgtgtcatgc catggcctgg gactagttct 1620

-continued

```
agagcaccgg tgggcccgaa gatctggatc ccgaactgca ttagttatta atagtaatca   1680
attacggggt cattagttca tagcccatat atggagttcc gcgttacata acttacggta   1740
aatggcccgc ctggctgacc gcccaacgac ccccgcccat tgacgtcaat aatgacgtat   1800
gttcccatag taacgccaat agggactttc cattgacgtc aatgggtgga gtatttacgg   1860
taaactgccc acttggcagt acatcaagtg tatcatatgc caagtacgcc ccctattgac   1920
gtcaatgacg gtaaatggcc cgcctggcat tatgcccagt acatgacctt atgggacttt   1980
cctacttggc agtacatcta cgtattagtc atcgctatta ccatggtgat gcggttttgg   2040
cagtacatca atgggcgtgg atagcggttt gactcacggg gatttccaag tctccacccc   2100
attgacgtca atgggagttt gttttggcac caaaatcaac gggactttcc aaaatgtcgt   2160
aacaactccg ccccattgac gcaaatgggc ggtaggcgtg tacggtggga ggtctatata   2220
agcagagctg gtttagtgaa ccgtcagatc cgctagcctt ggggtacccc ggccggccgg   2280
cgcgccacgc gtcgaagaag gtgagtaatc ttaacatgct cttttttttt tttttgcta   2340
atccctttg tgtgctgatg ttaggatgac atttacaaca aatgtttgtt cctgacagga   2400
aaaaccttgc tgggtacctt cgttgccgga cacttcttgt cctctacttt ggaaaaaagg   2460
aattgagagc ccaattggcc accatgagat ctggcgaccc cgtggtgctg cagaggaggg   2520
actgggagaa ccccggcgtg acccagctga acaggctggc cgcccacccc cccttcgcca   2580
gctggaggaa cagcgaggag gccaggaccg acaggcccag ccagcagctg aggagcctga   2640
acggcgagtg gaggttcgcc tggttccccg cccccgaggc cgtgcccgag agctggctgg   2700
agtgcgacct gcccgaggcc gacaccgtgg tggtgcccag caactggcag atgcacggct   2760
acgacgcccc catctacacc aacgtgacct accccatcac cgtgaacccc cccttcgtgc   2820
ccaccgagaa ccccaccggc tgctacagcc tgaccttcaa cgtggacgag agctggctgc   2880
aggagggcca gaccaggatc atcttcgacg gcgtgaacag cgccttccac ctgtggtgca   2940
acggcaggtg ggtgggctac ggccaggaca gcaggctgcc cagcgagttc gacctgagcg   3000
ccttcctgag ggctggcgag aacaggctgg ccgtgatggt gctgaggtgg agcgacggca   3060
gctacctgga ggaccaggat atgtggagga tgagcggcat cttcagggac gtgagcctgc   3120
tgcacaagcc caccacccag atcagcgact tccatgtggc caccaggttc aacgacgact   3180
tcagcagggc cgtgctggag gccgaggtgc agatgtgcgg cgagctgagg gactacctga   3240
gggtgaccgt gagcctgtgg cagggcgaga cccaggtggc cagcggcacc gccccccttcg   3300
gcggcgagat catcgacgag aggggcggct acgccgacag ggtgaccctg aggctgaacg   3360
tggagaaccc caagctgtgg agcgccgaga tccccaacct gtacagggcc gtggtggagc   3420
tgcacaccgc cgacggcacc ctgatcgagg ccgaagcctg cgacgtgggc ttcagggagg   3480
tgaggatcga gaacggcctg ctgctgctga acggcaagcc cctgctgatc aggggcgtga   3540
acaggcacga gcaccacccc ctgcacggcc aggtgatgga cgagcagaca atggtgcagg   3600
acatcctgct gatgaagcag aacaacttca acgccgtgag gtgcagccac taccccaacc   3660
acccccctgtg gtacaccctg tgcgacaggt acggcctgta cgtggtggac gaggccaaca   3720
tcgagaccca cggcatggtg cccatgaaca ggctgaccga cgaccccagg tggctgcccg   3780
ccatgagcga gagggtgacc aggatggtgc agagggacag gaaccacccc agcgtgatca   3840
tctggagcct gggcaacgag agcggccacg gcgccaacca cgacgccctg tacaggtgga   3900
tcaagagcgt ggaccccagc aggcccgtgc agtacgaggg cggcggcgcc gacaccaccg   3960
ccaccgacat catctgcccc atgtacgcca gggtggacga ggaccagccc ttccccgccg   4020
```

-continued

```
tgcccaagtg gagcatcaag aagtggctga gcctgcccgg cgagaccagg cccctgatcc   4080
tgtgcgagta cgcccacgct atgggcaaca gcctgggcgg cttcgccaag tactggcaag   4140
ccttcaggca gtaccccagg ctgcagggcg gcttcgtgtg ggactgggtg gaccagagcc   4200
tgatcaagta cgacgagaac ggcaacccct ggagcgccta cggcggcgac ttcggcgaca   4260
cccccaacga caggcagttc tgcatgaacg gcctggtgtt cgccgacagg accccccacc   4320
ccgccctgac cgaggccaag caccagcagc agttcttcca gttcaggctg agcggccaga   4380
ccatcgaggt gaccagcgag tacctgttca ggcacagcga caacgagctg ctgcactgga   4440
tggtggccct ggacggcaag cccctggcca gcggcgaggt gcccctggac gtggcccccc   4500
agggcaagca gctgatcgag ctgcccgagc tgccccagcc cgagagcgcc ggacagctgt   4560
ggctgaccgt gagggtggtg cagcccaacg ccaccgcctg gagcgaggct ggccacatca   4620
gcgcctggca gcagtggagg ctggccgaga acctgagcgt gaccctgccc gccgccagcc   4680
acgccatccc ccacctgacc acaagcgaga tggacttctg catcgagctg ggcaacaaga   4740
ggtggcagtt caacaggcag agcggcttcc tgagccagat gtggatcggc gacaagaagc   4800
agctgctgac cccccctgagg gaccagttca ccagggcccc cctggacaac gacatcggcg   4860
tgagcgaggc caccaggatc gaccccaacg cctgggtgga gaggtggaag gccgctggcc   4920
actaccaggc cgaggccgcc ctgctgcagt gtaccgccga caccctggcc gacgccgtgc   4980
tgatcaccac cgcccacgcc tggcagcacc agggcaagac cctgttcatc agcaggaaga   5040
cctacaggat cgacggcagc ggccagatgg ctatcaccgt ggacgtggag gtggccagcg   5100
acaccccccca ccccgccagg atcggcctga actgccagct ggcccaggtg gccgagaggg   5160
tgaactggct gggcctgggc ccccaggaga actaccccga caggctgacc gccgcctgct   5220
tcgacaggtg ggacctgccc ctgagcgata tgtacacccc ctacgtgttc cccagcgaga   5280
acggcctgag gtgcggcacc agggagctga actacggccc ccaccagtgg aggggcgact   5340
tccagttcaa catcagcagg tacagccagc agcagctgat ggagaccagc cacaggcacc   5400
tgctgcacgc cgaggagggc acctggctga acatcgacgg cttccacatg ggcatcggcg   5460
gcgacgacag ctggagcccc agcgtgagcg ccgagttcca gctgagcgct ggcagatacc   5520
actaccagct ggtgtggtgc cagaagtaac atatgtgact aactaggtac gtagcggccg   5580
cgtcgacgat caggtaagtg tacccaattc gccctatagt gagtcgtatt acaattcact   5640
cgatcgccct tcccaacagt tgcgcagcct gaatggcgaa tggagatcca atttttaagt   5700
gtataatgtg ttaaactact gattctaatt gtttgtgtat tttagattca cagtcccaag   5760
gctcatttca ggcccctcag tcctcacagt ctgttcatga tcataatcag ccataccaca   5820
tttgtagagg ttttacttgc tttaaaaaac ctcccacacc tcccccctgaa cctgaaacat   5880
aaaatgaatg caattgttgt tgttaacttg tttattgcag cttataatgg ttacaaataa   5940
agcaatagca tcacaaattt cacaaataaa gcattttttt cactgcattc tagttgtggt   6000
ttgtccaaac tcatcaatgt atcttaacgc gctgatttaa atcggtccgc gtacgatgca   6060
tattaccctg ttatccctac cgcggttact ggccgtcgtt ttacaacgtc gtgactggga   6120
aaaccctggc gatgctcttc tcccggtgaa aacctctgac acatggctct tctaaatccg   6180
gagtttaaac gcttccttca tgtgagcaaa aggccagcaa aaggccagga accgtaaaaa   6240
ggccgcgttg ctggcgtttt tccataggct ccgccccccct gacgagcatc acaaaaatcg   6300
acgctcaagt cagaggtggc gaaacccgac aggactataa agataccagg cgtttccccc   6360
```

-continued

```
tggaagctcc ctcgtgcgct ctcctgttcc gaccctgccg cttaccggat acctgtccgc   6420

ctttctccct tcgggaagcg tggcgctttc tcatagctca cgctgtaggt atctcagttc   6480

ggtgtaggtc gttcgctcca agctgggctg tgtgcacgaa ccccccgttc agcccgaccg   6540

ctgcgcctta tccggtaact atcgtcttga gtccaacccg gtaagacacg acttatcgcc   6600

actggcagca gccactggta acaggattag cagagcgagg tatgtaggcg gtgctacaga   6660

gttcttgaag tggtggccta actacggcta cactagaagg acagtatttg gtatctgcgc   6720

tctgctgaag ccagttacct tcggaaaaag agttggtagc tcttgatccg gcaaacaaac   6780

caccgctggt agcggtggtt tttttgtttg caagcagcag attacgcgca gaaaaaaagg   6840

atctcaagaa gatcctttga tcttttctac ggggtctgac gctcagtgga acgaaaactc   6900

acgttaaggg attttggtca tgcctaggtg gcaaacagct attatgggta ttatgggtct   6960

accggtgcat gagattatca aaaaggatct tcacctagat ccttttaaat taaaaatgaa   7020

gttttaaatc aatctaaagt atatatgagt aaacttggtc tgacagttac caatgcttaa   7080

tcagtgaggc acctatctca gcgatctgtc tatttcgttc atccatagtt gcctgactcc   7140

ccgtcgtgta gataactacg atacgggagg gcttaccatc tggccccagt gctgcaatga   7200

taccgcgaga cccacgctca ccggctccag atttatcagc aataaaccag ccagccggaa   7260

gggccgagcg cagaagtggt cctgcaactt tatccgcctc catccagtct attaattgtt   7320

gccgggaagc tagagtaagt agttcgccag ttaatagttt gcgcaacgtt gttgccattg   7380

ctacaggcat cgtggtgtca cgctcgtcgt ttggtatggc ttcattcagc tccggttccc   7440

aacgatcaag gcgagttaca tgatccccca tgttgtgcaa aaaagcggtt agctccttcg   7500

gtcctccgat cgttgtcaga agtaagttgg ccgcagtgtt atcactcatg gttatggcag   7560

cactgcataa ttctcttact gtcatgccat ccgtaagatg cttttctgtg actggtgagt   7620

actcaaccaa gtcattctga gaatagtgta tgcggcgacc gagttgctct tgcccggcgt   7680

caatacggga taataccgcg ccacatagca gaactttaaa agtgctcatc attggaaaac   7740

gttcttcggg gcgaaaactc tcaaggatct taccgctgtt gagatccagt tcgatgtaac   7800

ccactcgtgc acccaactga tcttcagcat cttttacttt caccagcgtt tctgggtgag   7860

caaaaacagg aaggcaaaat gccgcaaaaa agggaataag ggcgacacgg aaatgttgaa   7920

tactcatact cttccttttt caatattatt gaagcattta tcagggttat tgtctcggga   7980

gcggatacat atttgaatgt atttagaaaa a                                  8011
```

<210> SEQ ID NO 13
<211> LENGTH: 8011
<212> TYPE: DNA
<213> ORGANISM: Artificial
<220> FEATURE:
<223> OTHER INFORMATION: synthetic

<400> SEQUENCE: 13

```
taaacaaata ggggttccgc gcacatttcc ccgaaaagtg ccacctgacg tcacctggtc     60

ttaagggcta tggcagggcc tgccgccccg acgttggctg cgagccctgg gccttcaccc    120

gaacttgggg ggtggggtgg ggaaaaggaa gaaacgcggg cgtattggcc ccaatggggt    180

ctcggtgggg tatcgacaga gtgccagccc tgggaccgaa ccccgcgttt atgaacaaac    240

gacccaacac cgtgcgtttt attctgtctt tttattgccg tcatagcgcg ggttccttcc    300

ggtattgtct ccttccgtgt ttcactcgag tcagaagaac tcgtcaagaa ggcgatagaa    360

ggcgatgcgc tgcgaatcgg gagcggcgat accgtaaagc acgaggaagc ggtcagccca    420
```

-continued

```
ttcgccgcca agctcttcag caatatcacg ggtagccaac gctatgtcct gatagcggtc    480
cgccacaccc agccggccac agtcgatgaa tccagaaaag cggccatttt ccaccatgat    540
attcggcaag caggcatcgc catgggtcac gacgagatcc tcgccgtcgg gcatgcgcgc    600
cttgagcctg gcgaacagtt cggctggcgc gagcccctga tgctcttcgt ccagatcatc    660
ctgatcgaca agaccggctt ccatccgagt acgtgctcgc tcgatgcgat gtttcgcttg    720
gtggtcgaat gggcaggtag ccggatcaag cgtatgcagc cgccgcattg catcagccat    780
gatggatact ttctcggcag gagcaaggtg agatgacagg agatcctgcc ccggcacttc    840
gcccaatagc agccagtccc ttcccgcttc agtgacaacg tcgagcacag ctgcgcaagg    900
aacgcccgtc gtggccagcc acgatagccg cgctgcctcg tcctgcagtt cattcagggc    960
accggacagg tcggtcttga caaaaagaac cgggcgcccc tgcgctgaca gccggaacac   1020
ggcggcatca gagcagccga ttgtctgttg tgcccagtca tagccgaata gcctctccac   1080
ccaagcggcc ggagaacctg cgtgcaatcc atcttgttca atggccgatc ccatggtggc   1140
tctagaggaa tagctcagag gccgaggcgg cttcggcctc tgcataaata aaaaaaatta   1200
gtcagccatg gggcggagaa tgggcggaac tgggcggagt taggggcggg atgggcggag   1260
ttaggggcgg gactatggtt gctgactaat tgagatgcat gctttgcata cttctgcctg   1320
ctggggagcc tggggacttt ccacacctgg ttgctgacta attgagatgc atgctttgca   1380
tacttctgcc tgctggggag cctggggact ttccacaccc taacaagctt gcccgggcag   1440
cggataacaa tttcacacag gaaacagcta tgaccatgat tagctgagct aactataacg   1500
gtcctaaggt agcgaatcga tgcgatcgct taattaacct gcagggatat cccatggggg   1560
ccgcgagctc tcccccgggg gaacagcatg cgtgtcatgc catggcctgg gactagttct   1620
agagcaccgg tgggcccgaa gatctggatc ccgaactgca ttagttatta atagtaatca   1680
attacggggt cattagttca tagcccatat atggagttcc gcgttacata acttacggta   1740
aatggcccgc ctggctgacc gcccaacgac ccccgcccat tgacgtcaat aatgacgtat   1800
gttcccatag taacgccaat agggactttc cattgacgtc aatgggtgga gtatttacgg   1860
taaactgccc acttggcagt acatcaagtg tatcatatgc caagtacgcc ccctattgac   1920
gtcaatgacg gtaaatggcc cgcctggcat tatgcccagt acatgacctt atgggacttt   1980
cctacttggc agtacatcta cgtattagtc atcgctatta ccatggtgat gcggttttgg   2040
cagtacatca atgggcgtgg atagcggttt gactcacggg gatttccaag tctccacccc   2100
attgacgtca atgggagttt gttttggcac caaaatcaac gggactttcc aaaatgtcgt   2160
aacaactccg ccccattgac gcaaatgggc ggtaggcgtg tacggtggga ggtctatata   2220
agcagagctg gtttagtgaa ccgtcagatc cgctagcctt ggggtacccc ggccggccgg   2280
cgcgccacgc gtcgaagaag gtgagtaatc ttaacatgct cttttttttt ttttttttta   2340
atccctttttg tgtgctgatg ttaggatgac atttacaaca aatgtttgtt cctgacagga   2400
aaaaccttgc tgggtacctt cgttgccgga cacttcttgt cctctacttt ggaaaaaagg   2460
aattgagagc ccaattggcc accatgagat ctggcgaccc cgtggtgctg cagaggaggg   2520
actgggagaa ccccggcgtg acccagctga acaggctggc cgcccacccc cccttcgcca   2580
gctggaggaa cagcgaggag gccaggaccg acaggcccag ccagcagctg aggagcctga   2640
acggcgagtg gaggttcgcc tggttccccg cccccgaggc cgtgcccgag agctggctgg   2700
agtgcgacct gcccgaggcc gacaccgtgg tggtgcccag caactggcag atgcacggct   2760
```

-continued

```
acgacgcccc catctacacc aacgtgacct accccatcac cgtgaacccc cccttcgtgc   2820
ccaccgagaa ccccaccggc tgctacagcc tgaccttcaa cgtggacgag agctggctgc   2880
aggagggcca gaccaggatc atcttcgacg gcgtgaacag cgccttccac ctgtggtgca   2940
acggcaggtg ggtgggctac ggccaggaca gcaggctgcc cagcgagttc gacctgagcg   3000
ccttcctgag ggctggcgag aacaggctgg ccgtgatggt gctgaggtgg agcgacggca   3060
gctacctgga ggaccaggat atgtggagga tgagcggcat cttcagggac gtgagcctgc   3120
tgcacaagcc caccacccag atcagcgact tccatgtggc caccaggttc aacgacgact   3180
tcagcagggc cgtgctggag gccgaggtgc agatgtgcgg cgagctgagg gactacctga   3240
gggtgaccgt gagcctgtgg cagggcgaga cccaggtggc cagcggcacc gccccccttcg   3300
gcggcgagat catcgacgag aggggcggct acgccgacag ggtgaccctg aggctgaacg   3360
tggagaaccc caagctgtgg agcgccgaga tccccaacct gtacagggcc gtggtggagc   3420
tgcacaccgc cgacggcacc ctgatcgagg ccgaagcctg cgacgtgggc ttcagggagg   3480
tgaggatcga gaacggcctg ctgctgctga acggcaagcc cctgctgatc aggggcgtga   3540
acaggcacga gcaccacccc ctgcacggcc aggtgatgga cgagcagaca atggtgcagg   3600
acatcctgct gatgaagcag aacaacttca acgccgtgag gtgcagccac taccccaacc   3660
acccccctgtg gtacaccctg tgcgacaggt acggcctgta cgtggtggac gaggccaaca   3720
tcgagaccca cggcatggtg cccatgaaca ggctgaccga cgaccccagg tggctgcccg   3780
ccatgagcga gagggtgacc aggatggtgc agagggacag gaaccacccc agcgtgatca   3840
tctggagcct gggcaacgag agcggccacg gcgccaacca cgacgccctg tacaggtgga   3900
tcaagagcgt ggaccccagc aggcccgtgc agtacgaggg cggcggcgcc gacaccaccg   3960
ccaccgacat catctgcccc atgtacgcca gggtggacga ggaccagccc ttccccgccg   4020
tgcccaagtg gagcatcaag aagtggctga gcctgcccgg cgagaccagg cccctgatcc   4080
tgtgcgagta cgcccacgct atgggcaaca gcctgggcgg cttcgccaag tactggcaag   4140
ccttcaggca gtaccccagg ctgcagggcg gcttcgtgtg ggactgggtg gaccagagcc   4200
tgatcaagta cgacgagaac ggcaacccct ggagcgccta cggcggcgac ttcggcgaca   4260
cccccaacga caggcagttc tgcatgaacg gcctggtgtt cgccgacagg accccccacc   4320
ccgccctgac cgaggccaag caccagcagc agttcttcca gttcaggctg agcggccaga   4380
ccatcgaggt gaccagcgag tacctgttca ggcacagcga caacgagctg ctgcactgga   4440
tggtggccct ggacggcaag cccctggcca gcggcgaggt gcccctggac gtggcccccc   4500
agggcaagca gctgatcgag ctgcccgagc tgccccagcc cgagagcgcc ggacagctgt   4560
ggctgaccgt gagggtggtg cagcccaacg ccaccgcctg gagcgaggct ggccacatca   4620
gcgcctggca gcagtggagg ctggccgaga acctgagcgt gaccctgccc gccgccagcc   4680
acgccatccc ccacctgacc acaagcgaga tggacttctg catcgagctg ggcaacaaga   4740
ggtggcagtt caacaggcag agcggcttcc tgagccagat gtggatcggc gacaagaagc   4800
agctgctgac ccccctgagg gaccagttca ccagggcccc cctggacaac gacatcggcg   4860
tgagcgaggc caccaggatc gaccccaacg cctgggtgga gaggtggaag gccgctggcc   4920
actaccaggc cgaggccgcc ctgctgcagt gtaccgccga caccctggcc gacgccgtgc   4980
tgatcaccac cgcccacgcc tggcagcacc agggcaagac cctgttcatc agcaggaaga   5040
cctacaggat cgacggcagc ggccagatgg ctatcaccgt ggacgtggag gtggccagcg   5100
acaccccccca ccccgccagg atcggcctga actgccagct ggcccaggtg gccgagaggg   5160
```

```
tgaactggct gggcctgggc ccccaggaga actaccccga caggctgacc gccgcctgct   5220
tcgacaggtg ggacctgccc ctgagcgata tgtacacccc ctacgtgttc cccagcgaga   5280
acggcctgag gtgcggcacc agggagctga actacggccc ccaccagtgg aggggcgact   5340
tccagttcaa catcagcagg tacagccagc agcagctgat ggagaccagc cacaggcacc   5400
tgctgcacgc cgaggagggc acctggctga acatcgacgg cttccacatg ggcatcggcg   5460
gcgacgacag ctggagcccc agcgtgagcg ccgagttcca gctgagcgct ggcagatacc   5520
actaccagct ggtgtggtgc cagaagtaac atatgtgact aactaggtac gtagcggccg   5580
cgtcgacgat caggtaagtg tacccaattc gccctatagt gagtcgtatt acaattcact   5640
cgatcgccct tcccaacagt tgcgcagcct gaatggcgaa tggagatcca atttttaagt   5700
gtataatgtg ttaaactact gattctaatt gtttgtgtat tttagattca cagtcccaag   5760
gctcatttca ggcccctcag tcctcacagt ctgttcatga tcataatcag ccataccaca   5820
tttgtagagg ttttacttgc tttaaaaaac ctcccacacc tccccctgaa cctgaaacat   5880
aaaatgaatg ccattgttgt tgttaacttg tttattgcag cttataatgg ttacaaataa   5940
agcaatagca tcacaaattt cacaaataaa gcattttttt cactgcattc tagttgtggt   6000
ttgtccaaac tcatcaatgt atcttaacgc gctgatttaa atcggtccgc gtacgatgca   6060
tattaccctg ttatccctac cgcggttact ggccgtcgtt ttacaacgtc gtgactggga   6120
aaaccctggc gatgctcttc tcccggtgaa aacctctgac acatggctct tctaaatccg   6180
gagtttaaac gcttccttca tgtgagcaaa aggccagcaa aaggccagga accgtaaaaa   6240
ggccgcgttg ctggcgtttt tccataggct ccgcccccct gacgagcatc acaaaaatcg   6300
acgctcaagt cagaggtggc gaaacccgac aggactataa agataccagg cgtttccccc   6360
tggaagctcc ctcgtgcgct ctcctgttcc gaccctgccg cttaccggat acctgtccgc   6420
ctttctccct tcgggaagcg tggcgctttc tcatagctca cgctgtaggt atctcagttc   6480
ggtgtaggtc gttcgctcca agctgggctg tgtgcacgaa ccccccgttc agcccgaccg   6540
ctgcgcctta tccggtaact atcgtcttga gtccaacccg gtaagacacg acttatcgcc   6600
actggcagca gccactggta acaggattag cagagcgagg tatgtaggcg gtgctacaga   6660
gttcttgaag tggtggccta actacggcta cactagaagg acagtatttg gtatctgcgc   6720
tctgctgaag ccagttacct tcggaaaaag agttggtagc tcttgatccg gcaaacaaac   6780
caccgctggt agcggtggtt tttttgtttg caagcagcag attacgcgca gaaaaaaagg   6840
atctcaagaa gatcctttga tcttttctac ggggtctgac gctcagtgga acgaaaactc   6900
acgttaaggg attttggtca tgcctaggtg gcaaacagct attatgggta ttatgggtct   6960
accggtgcat gagattatca aaaaggatct tcacctagat ccttttaaat taaaaatgaa   7020
gttttaaatc aatctaaagt atatatgagt aaacttggtc tgacagttac caatgcttaa   7080
tcagtgaggc acctatctca gcgatctgtc tatttcgttc atccatagtt gcctgactcc   7140
ccgtcgtgta gataactacg atacgggagg gcttaccatc tggccccagt gctgcaatga   7200
taccgcgaga cccacgctca ccggctccag atttatcagc aataaaccag ccagccggaa   7260
gggccgagcg cagaagtggt cctgcaactt tatccgcctc catccagtct attaattgtt   7320
gccgggaagc tagagtaagt agttcgccag ttaatagttt gcgcaacgtt gttgccattg   7380
ctacaggcat cgtggtgtca cgctcgtcgt ttggtatggc ttcattcagc tccggttccc   7440
aacgatcaag gcgagttaca tgatccccca tgttgtgcaa aaaagcggtt agctccttcg   7500
```

```
gtcctccgat cgttgtcaga agtaagttgg ccgcagtgtt atcactcatg gttatggcag   7560
cactgcataa ttctcttact gtcatgccat ccgtaagatg cttttctgtg actggtgagt   7620
actcaaccaa gtcattctga gaatagtgta tgcggcgacc gagttgctct tgcccggcgt   7680
caatacggga taataccgcg ccacatagca gaactttaaa agtgctcatc attggaaaac   7740
gttcttcggg gcgaaaactc tcaaggatct taccgctgtt gagatccagt tcgatgtaac   7800
ccactcgtgc acccaactga tcttcagcat cttttacttt caccagcgtt tctgggtgag   7860
caaaaacagg aaggcaaaat gccgcaaaaa agggaataag ggcgacacgg aaatgttgaa   7920
tactcatact cttccttttt caatattatt gaagcattta tcagggttat tgtctcggga   7980
gcggatacat atttgaatgt atttagaaaa a                                  8011
```

<210> SEQ ID NO 14
<211> LENGTH: 7844
<212> TYPE: DNA
<213> ORGANISM: Artificial
<220> FEATURE:
<223> OTHER INFORMATION: synthetic

<400> SEQUENCE: 14

```
taaacaaata ggggttccgc gcacatttcc ccgaaaagtg ccacctgacg tcacctggtc     60
ttaagggcta tggcagggcc tgccgccccg acgttggctg cgagccctgg gccttcaccc    120
gaacttgggg ggtggggtgg ggaaaaggaa gaaacgcggg cgtattggcc ccaatggggt    180
ctcggtgggg tatcgacaga gtgccagccc tgggaccgaa ccccgcgttt atgaacaaac    240
gacccaacac cgtgcgtttt attctgtctt tttattgccg tcatagcgcg ggttccttcc    300
ggtattgtct ccttccgtgt ttcactcgag tcagaagaac tcgtcaagaa ggcgatagaa    360
ggcgatgcgc tgcgaatcgg gagcggcgat accgtaaagc acgaggaagc ggtcagccca    420
ttcgccgcca agctcttcag caatatcacg ggtagccaac gctatgtcct gatagcggtc    480
cgccacaccc agccggccac agtcgatgaa tccagaaaag cggccatttt ccaccatgat    540
attcggcaag caggcatcgc catgggtcac gacgagatcc tcgccgtcgg gcatgcgcgc    600
cttgagcctg gcgaacagtt cggctggcgc gagcccctga tgctcttcgt ccagatcatc    660
ctgatcgaca agaccggctt ccatccgagt acgtgctcgc tcgatgcgat gtttcgcttg    720
gtggtcgaat gggcaggtag ccggatcaag cgtatgcagc cgccgcattg catcagccat    780
gatggatact ttctcggcag gagcaaggtg agatgacagg agatcctgcc ccggcacttc    840
gcccaatagc agccagtccc ttcccgcttc agtgacaacg tcgagcacag ctgcgcaagg    900
aacgcccgtc gtggccagcc acgatagccg cgctgcctcg tcctgcagtt cattcagggc    960
accggacagg tcggtcttga caaaaagaac cgggcgcccc tgcgctgaca gccggaacac   1020
ggcggcatca gagcagccga ttgtctgttg tgcccagtca tagccgaata gcctctccac   1080
ccaagcggcc ggagaacctg cgtgcaatcc atcttgttca atggccgatc ccatggtggc   1140
tctagaggaa tagctcagag gccgaggcgg cttcggcctc tgcataaata aaaaaaatta   1200
gtcagccatg gggcggagaa tgggcggaac tgggcggagt taggggcggg atgggcggag   1260
ttaggggcgg gactatggtt gctgactaat tgagatgcat gctttgcata cttctgcctg   1320
ctggggagcc tggggacttt ccacacctgg ttgctgacta attgagatgc atgctttgca   1380
tacttctgcc tgctggggag cctggggact ttccacaccc taacaagctt gcccgggcag   1440
cggataacaa tttcacacag gaaacagcta tgaccatgat tagctgagct aactataacg   1500
gtcctaaggt agcgaatcga tgcgatcgct taattaacct gcagggatat cccatggggg   1560
```

-continued

```
ccgcgagctc tcccccgggg gaacagcatg cgtgtcatgc catggcctgg gactagttct   1620
agagcaccgg tgggcccgaa gatctggatc ccgaactgca ttagttatta atagtaatca   1680
attacggggt cattagttca tagcccatat atggagttcc gcgttacata acttacggta   1740
aatggcccgc ctggctgacc gcccaacgac ccccgcccat tgacgtcaat aatgacgtat   1800
gttcccatag taacgccaat agggactttc cattgacgtc aatgggtgga gtatttacgg   1860
taaactgccc acttggcagt acatcaagtg tatcatatgc caagtacgcc ccctattgac   1920
gtcaatgacg gtaaatggcc cgcctggcat tatgcccagt acatgacctt atgggacttt   1980
cctacttggc agtacatcta cgtattagtc atcgctatta ccatggtgat gcggttttgg   2040
cagtacatca atgggcgtgg atagcggttt gactcacggg gatttccaag tctccacccc   2100
attgacgtca atgggagttt gttttggcac caaaatcaac gggactttcc aaaatgtcgt   2160
aacaactccg ccccattgac gcaaatgggc ggtaggcgtg tacggtggga ggtctatata   2220
agcagagctg gtttagtgaa ccgtcagatc cgctagcctt ggggtacccc ggccggccgg   2280
cgcgccacgc gtgggggggg ggggcaattg gccaccatga gatctggcga ccccgtggtg   2340
ctgcagagga gggactggga gaaccccggc gtgacccagc tgaacaggct ggccgcccac   2400
ccccccttcg ccagctggag gaacagcgag gaggccagga ccgacaggcc cagccagcag   2460
ctgaggagcc tgaacggcga gtggaggttc gcctggttcc ccgcccccga ggccgtgccc   2520
gagagctggc tggagtgcga cctgcccgag gccgacaccg tggtggtgcc cagcaactgg   2580
cagatgcacg gctacgacgc ccccatctac accaacgtga cctaccccat caccgtgaac   2640
ccccccttcg tgcccaccga gaaccccacc ggctgctaca gcctgacctt caacgtggac   2700
gagagctggc tgcaggaggg ccagaccagg atcatcttcg acggcgtgaa cagcgccttc   2760
cacctgtggt gcaacggcag gtgggtgggc tacggccagg acagcaggct gcccagcgag   2820
ttcgacctga gcgccttcct gagggctggc gagaacaggc tggccgtgat ggtgctgagg   2880
tggagcgacg gcagctacct ggaggaccag gatatgtgga ggatgagcgg catcttcagg   2940
gacgtgagcc tgctgcacaa gcccaccacc cagatcagcg acttccatgt ggccaccagg   3000
ttcaacgacg acttcagcag ggccgtgctg gaggccgagg tgcagatgtg cggcgagctg   3060
agggactacc tgagggtgac cgtgagcctg tggcagggcg agacccaggt ggccagcggc   3120
accgccccct tcggcggcga gatcatcgac gagaggggcg gctacgccga cagggtgacc   3180
ctgaggctga acgtggagaa ccccaagctg tggagcgccg agatccccaa cctgtacagg   3240
gccgtggtgg agctgcacac cgccgacggc accctgatcg aggccgaagc ctgcgacgtg   3300
ggcttcaggg aggtgaggat cgagaacggc ctgctgctgc tgaacggcaa gcccctgctg   3360
atcaggggcg tgaacaggca cgagcaccac cccctgcacg gccaggtgat ggacgagcag   3420
acaatggtgc aggacatcct gctgatgaag cagaacaact tcaacgccgt gaggtgcagc   3480
cactacccca accaccccct gtggtacacc ctgtgcgaca ggtacggcct gtacgtggtg   3540
gacgaggcca acatcgagac ccacggcatg gtgcccatga acaggctgac cgacgacccc   3600
aggtggctgc ccgccatgag cgagagggtg accaggatgg tgcagaggga caggaaccac   3660
cccagcgtga tcatctggag cctgggcaac gagagcggcc acggcgccaa ccacgacgcc   3720
ctgtacaggt ggatcaagag cgtggacccc agcaggcccg tgcagtacga gggcggcggc   3780
gccgacacca ccgccaccga catcatctgc cccatgtacg ccagggtgga cgaggaccag   3840
cccttccccg ccgtgcccaa gtggagcatc aagaagtggc tgagcctgcc cggcgagacc   3900
```

-continued aggcccctga tcctgtgcga gtacgcccac gctatgggca acagcctggg cggcttcgcc 3960
aagtactggc aagccttcag gcagtacccc aggctgcagg gcggcttcgt gtgggactgg 4020
gtggaccaga gcctgatcaa gtacgacgag aacggcaacc cctggagcgc ctacggcggc 4080
gacttcggcg acacccccaa cgacaggcag ttctgcatga acggcctggt gttcgccgac 4140
aggacccccc accccgccct gaccgaggcc aagcaccagc agcagttctt ccagttcagg 4200
ctgagcggcc agaccatcga ggtgaccagc gagtacctgt tcaggcacag cgacaacgag 4260
ctgctgcact ggatggtggc cctggacggc aagcccctgg ccagcggcga ggtgcccctg 4320
gacgtggccc cccagggcaa gcagctgatc gagctgcccg agctgcccca gcccgagagc 4380
gccggacagc tgtggctgac cgtgagggtg gtgcagccca acgccaccgc ctggagcgag 4440
gctggccaca tcagcgcctg gcagcagtgg aggctggccg agaacctgag cgtgaccctg 4500
cccgccgcca gccacgccat cccccacctg accacaagcg agatggactt ctgcatcgag 4560
ctgggcaaca agaggtggca gttcaacagg cagagcggct tcctgagcca gatgtggatc 4620
ggcgacaaga agcagctgct gacccccctg agggaccagt tcaccagggc cccccctggac 4680 aacgacatcg gcgtgagcga ggccaccagg atcgacccca acgcctgggt ggagaggtgg 4740
aaggccgctg gccactacca ggccgaggcc gccctgctgc agtgtaccgc cgacaccctg 4800
gccgacgccg tgctgatcac caccgcccac gcctggcagc accagggcaa gaccctgttc 4860
atcagcagga agacctacag gatcgacggc agcggccaga tggctatcac cgtggacgtg 4920
gaggtggcca gcgacacccc ccaccccgcc aggatcggcc tgaactgcca gctggcccag 4980
gtggccgaga gggtgaactg gctgggcctg ggcccccagg agaactaccc cgacaggctg 5040
accgccgcct gcttcgacag gtgggacctg cccctgagcg atatgtacac cccctacgtg 5100
ttccccagcg agaacggcct gaggtgcggc accagggagc tgaactacgg cccccaccag 5160
tggaggggcg acttccagtt caacatcagc aggtacagcc agcagcagct gatggagacc 5220
agccacaggc acctgctgca cgccgaggag ggcacctggc tgaacatcga cggcttccac 5280
atgggcatcg gcggcgacga cagctggagc cccagcgtga gcgccgagtt ccagctgagc 5340
gctggcagat accactacca gctggtgtgg tgccagaagt aacatatgtg actaactagg 5400
tacgtagcgg ccgcgtcgac gatcaggtaa gtgtacccaa ttcgccctat agtgagtcgt 5460
attacaattc actcgatcgc ccttcccaac agttgcgcag cctgaatggc gaatggagat 5520
ccaattttta agtgtataat gtgttaaact actgattcta attgtttgtg tattttagat 5580
tcacagtccc aaggctcatt tcaggcccct cagtcctcac agtctgttca tgatcataat 5640
cagccatacc acatttgtag aggttttact tgctttaaaa aacctcccac acctccccct 5700
gaacctgaaa cataaaatga atgccattgt tgttgttaac ttgtttattg cagcttataa 5760
tggttacaaa taaagcaata gcatcacaaa tttcacaaat aaagcatttt tttcactgca 5820
ttctagttgt ggtttgtcca aactcatcaa tgtatcttaa cgcgctgatt taaatcggtc 5880
cgcgtacgat gcatattacc ctgttatccc taccgcggtt actggccgtc gttttacaac 5940
gtcgtgactg ggaaaaccct ggcgatgctc ttctcccggt gaaaacctct gacacatggc 6000
tcttctaaat ccggagttta aacgcttcct tcatgtgagc aaaaggccag caaaaggcca 6060
ggaaccgtaa aaaggccgcg ttgctggcgt ttttccatag gctccgcccc cctgacgagc 6120
atcacaaaaa tcgacgctca agtcagaggt ggcgaaaccc gacaggacta taaagatacc 6180
aggcgtttcc ccctggaagc tccctcgtgc gctctcctgt tccgaccctg ccgcttaccg 6240
gatacctgtc cgcctttctc ccttcgggaa gcgtggcgct ttctcatagc tcacgctgta 6300
ggtatctcag ttcggtgtag gtcgttcgct ccaagctggg ctgtgtgcac gaaccccccg 6360
ttcagcccga ccgctgcgcc ttatccggta actatcgtct tgagtccaac ccggtaagac 6420
acgacttatc gccactggca gcagccactg gtaacaggat tagcagagcg aggtatgtag 6480
gcggtgctac agagttcttg aagtggtggc ctaactacgg ctacactaga aggacagtat 6540
ttggtatctg cgctctgctg aagccagtta ccttcggaaa aagagttggt agctcttgat 6600
ccggcaaaca aaccaccgct ggtagcggtg gtttttttgt ttgcaagcag cagattacgc 6660
gcagaaaaaa aggatctcaa gaagatcctt tgatcttttc tacggggtct gacgctcagt 6720
ggaacgaaaa ctcacgttaa gggattttgg tcatgcctag gtggcaaaca gctattatgg 6780
gtattatggg tctaccggtg catgagatta tcaaaaagga tcttcaccta gatcctttta 6840
aattaaaaat gaagttttaa atcaatctaa agtatatatg agtaaacttg gtctgacagt 6900
taccaatgct taatcagtga ggcacctatc tcagcgatct gtctatttcg ttcatccata 6960
gttgcctgac tccccgtcgt gtagataact acgatacggg agggcttacc atctggcccc 7020
agtgctgcaa tgataccgcg agacccacgc tcaccggctc cagatttatc agcaataaac 7080
cagccagccg gaagggccga gcgcagaagt ggtcctgcaa ctttatccgc ctccatccag 7140
tctattaatt gttgccggga agctagagta agtagttcgc cagttaatag tttgcgcaac 7200
gttgttgcca ttgctacagg catcgtggtg tcacgctcgt cgtttggtat ggcttcattc 7260
agctccggtt cccaacgatc aaggcgagtt acatgatccc ccatgttgtg caaaaaagcg 7320
gttagctcct tcggtcctcc gatcgttgtc agaagtaagt tggccgcagt gttatcactc 7380
atggttatgg cagcactgca taattctctt actgtcatgc catccgtaag atgcttttct 7440
gtgactggtg agtactcaac caagtcattc tgagaatagt gtatgcggcg accgagttgc 7500
tcttgcccgg cgtcaatacg ggataatacc gcgccacata gcagaacttt aaaagtgctc 7560
atcattggaa aacgttcttc ggggcgaaaa ctctcaagga tcttaccgct gttgagatcc 7620
agttcgatgt aacccactcg tgcacccaac tgatcttcag catcttttac tttcaccagc 7680
gtttctgggt gagcaaaaac aggaaggcaa aatgccgcaa aaaagggaat aagggcgaca 7740
cggaaatgtt gaatactcat actcttcctt tttcaatatt attgaagcat ttatcagggt 7800
tattgtctcg ggagcggata catatttgaa tgtatttaga aaaa 7844

<210> SEQ ID NO 15
<211> LENGTH: 101
<212> TYPE: DNA
<213> ORGANISM: Equus caballus

<400> SEQUENCE: 15
agttaccggc tgaagaaggg aaaaccttgc tggaacttgt gattgagcag tttgaagact 60
tactagttag aattttattg ctggcagcat gtatatcttt t 101

<210> SEQ ID NO 16
<211> LENGTH: 375
<212> TYPE: DNA
<213> ORGANISM: Equus caballus

<400> SEQUENCE: 16
gtctaggtgt gtctttcaaa gacagcgatg attttaggaa ttctttttag aaagatagag 60
tgctaacgtg tttttttccc ccccctctgg acacgttgcc tggcgaattt ctacatcctg 120
cagagttacc ggctgaagaa ggtgagcgat ctgaacgtgt tcttccccg ctttgtgctg 180

-continued

```
atgttaagat gacgtttaca acagatgttt gtttctaaca gggaaaacct tgctggaact    240

tgtgattgag cagtttgaag acttactagt tagaatttta ttgctggcag catgtatatc    300

ttttgtaagt ataaagaaat ttattttgtc tccaaaaagt tgggaccgtt ccatagatga    360

aaagcgggga aagta                                                     375
```